(12) United States Patent
Solaiman et al.

(10) Patent No.: US 10,155,043 B2
(45) Date of Patent: Dec. 18, 2018

(54) COMPOSITIONS CONTAINING A BITTER TASTANT AND AT LEAST ONE SOPHOROLIPID, AND METHODS OF REDUCING BITTER TASTE ATTRIBUTED TO A BITTER TASTANT IN AN EDIBLE COMPOSITION

(71) Applicants: The United States of America, as Represented by the Secretary of Agriculture, Washington, DC (US); Monell Chemical Senses Center, Philadelphia, PA (US)

(72) Inventors: Daniel Solaiman, Dresher, PA (US); Richard D. Ashby, Glenside, PA (US); Mehmet Hakan Ozdener, Springfield, PA (US); Alexander Bachmanov, Philadelphia, PA (US)

(73) Assignees: The United States of America, as Represented by the Secretary of Agriculture, Washington, DC (US); Monell Chemical Senses Center, Philadelphia, PA (US)

( * ) Notice: Subject to any disclaimer, the term of this patent is extended or adjusted under 35 U.S.C. 154(b) by 9 days.

(21) Appl. No.: 15/388,615

(22) Filed: Dec. 22, 2016

(65) Prior Publication Data

US 2017/0189533 A1 Jul. 6, 2017

Related U.S. Application Data

(60) Provisional application No. 62/272,292, filed on Dec. 29, 2015.

(51) Int. Cl.
| | |
|---|---|
| *A61K 47/26* | (2006.01) |
| *A23L 27/00* | (2016.01) |
| *A23L 33/10* | (2016.01) |
| *A23K 20/158* | (2016.01) |

(52) U.S. Cl.
CPC .............. *A61K 47/26* (2013.01); *A23L 27/86* (2016.08); *A23L 33/10* (2016.08); *A23K 20/158* (2016.05); *A23V 2002/00* (2013.01)

(58) Field of Classification Search
CPC .................................. A23L 27/86; A61K 47/26
See application file for complete search history.

(56) References Cited

U.S. PATENT DOCUMENTS

| 2015/0094273 A1 | 4/2015 | Prabhune et al. |
| 2016/0280733 A1* | 9/2016 | Araki |

FOREIGN PATENT DOCUMENTS

| CN | 101019875 A | 8/2007 |
| CN | 101886047 A | 11/2010 |
| CN | 103275139 A | 9/2013 |
| EP | 2251002 A1 | 11/2010 |
| JP | 2014185105 A | 10/2014 |

OTHER PUBLICATIONS

Mousavi, Fereshteh et al., Production of Sophorolipid from an Identified Current Yeast, *Lachancea thermotolerans* BBMCZ7FA20, Isolated . . . ,(2015), Current Microbiology, 71(2):303-310.
International Searching Authority, PCT/US2016/068506 for the United States of America, as Represented by the Secretary of Agriculture, International Filing date Dec. 23, 2016.
Harjot et al., "Potential Biomedical and Pharmaceutical Applications of Microbial Surfants," World Journal of Pharmacy and Pharmaceutical Sciences, (2015), 4(04): 1557-1575.
Mona Mohamed Rashad et al., "Co-Utilization of Motor Oil Waste and Sunflower Oil Cake on the Production of New Sophorolipids by Candida bombicola NRRL Y-17069," Research Journal of Pharmaceutical, Biological and Chemical Sciences, (2014), pp. 1514-1528.
Karaman, Rafik, Prodrugs for Masking the Bitter Taste of Drugs, INTECH, (2014), Chapter 12.
Ley, Jakob P., Masking Bitter Taste by Molecules, Chem. Percept., (2008), 1:58-77.

* cited by examiner

*Primary Examiner* — Savitha M Rao
*Assistant Examiner* — Gregg Polansky
(74) *Attorney, Agent, or Firm* — John Fado; G. Byron Stover

(57) ABSTRACT

A composition comprising a bitter tastant and at least one sophorolipid and optionally a carrier; wherein the composition is edible and wherein the bitter taste of said bitter tastant is reduced. A method of reducing bitter taste attributed to a bitter tastant in an edible composition, said method comprising adding to said edible composition an effective amount of at least one sophorolipid and optionally a carrier; such that any bitter taste induced by the bitter tastant is reduced.

10 Claims, 15 Drawing Sheets

COMPOSITIONS CONTAINING A BITTER TASTANT AND AT LEAST ONE SOPHOROLIPID, AND METHODS OF REDUCING BITTER TASTE ATTRIBUTED TO A BITTER TASTANT IN AN EDIBLE COMPOSITION

REFERENCE TO RELATED APPLICATION

This application claims the benefit of U.S. Provisional Application No. 62/272,292 filed 29 Dec. 2015, which is incorporated herein by reference in their entirety.

BACKGROUND OF THE INVENTION

Sophorolipids (SLs) belong to the family of microbial glycolipids whose chemical structure imparts natural surfactancy. They are typically produced from renewable substrates by fermentation and provide the added benefits of biocompatibility and biodegradability (Develter, D. W. G., and L. M. L. Lauryssen, Eur. J. Lipid Sci. Technol., 112: 628-638 (2010)). Sophorolipids are typically made up of a disaccharide (sophorose; 2-O-β-D-glucopyranosyl-β-D glucopyranose) attached to a hydroxy fatty acid through a glycosidic linkage (FIG. 1). The specific location of those chemical bonds is dependent on the microbial strain used to produce the SLs. The most well-known SLs are naturally synthesized in high yields by the yeast *Candida bombicola* (Ashby, R. D., et al., Biotechnol. Lett., 30: 1093-1100 (2008)), and the glycosidic bond generally occurs between the 1' hydroxy group of the sophorose sugar and the ω or ω-1 carbon of the fatty acid. In these SLs, the 6' and 6" hydroxy groups of the sophorose are sites of potential acetylation and the fatty acid chain length varies between 16 (C-16) and 18 (C-18) carbons and may be saturated or unsaturated. Studies have shown that the preferred structural conformation of SLs produced by *C. bombicola* from glucose and palmitic acid (SL-p), oleic acid (SL-o) or stearic acid (SL-s) is as a lactone where the carboxylic acid group of the fatty acid is esterified to the disaccharide ring at carbon 4" (Nuñez, A., et al., Chromatographia, 53: 673-677 (2001)). Other strains of *Candida* such as *C. apicola* (Hommel, R. K., and K. Huse, Biotechnol. Lett., 33: 853-858 (1993)) and *C. batiste* (Konishi, M., et al., J. Oleo. Sci., 57: 359-369 (2008)) have been documented to synthesize SLs, and recently 3 new strains of *Candida* (*C. riodocensis*, *C. stellata* and *Candida* sp. Y-27208) were discovered to produce SLs with very little lactone form (Kurtzman, C. P., et al., FEMS Microbiol. Lett., 311: 140-146 (2010)). Another less well-known SL producer is the yeast *Rhodotorula bogoriensis* which generally produces SLs containing 13-hydroxydocosanoic acid (C-22) as the fatty acid moiety which is entirely in the free acid conformation (Nuñez, A., et al., Biotechnol. Lett., 26: 1087-1093 (2004); Cutler, A. J., and R. J. Light, J. Biol. Chem., 254: 1944-1950 (1979); Cutler, A. J., and R. J. Light, Can. J. Microbiol., 28: 223-230 (1982)).

Large production capacity from *C. bombicola* (reportedly as high as 422 g/L when using whey and rapeseed oil as substrates (Daniel, H.-J., et al., Biotechnol. Lett., 20: 1153-1156 (1998)) have increased awareness of SL applications (Solaiman, D. K. Y., et al., Inform, 15: 270-272 (2004)). Acetylated lactones have proven effective as additives in shampoos, body washes, and detergents (Hall, P., et al., U.S. Pat. No. 5,417,879; Inoue, S., et al., U.S. Pat. No. 4,215,213), and as emulsifiers for skin care products (Mager, H., et al., European Patent EP 0209783) and structured lipid emulsions (Xue, C.-L., et al., J. Am. Oil Chem. Soc., 90: 123-132 (2013)). In addition, they have been reported to have applications as food encapsulants (Allingham, R., U.S. Pat. No. 3,622,344), as degreasing agents (Hall et al. 1995), and to enhance soil bioremediation and waste water treatment (Makkar, R., and R. Cameotra, Appl. Microbiol. Biotechnol., 58: 428-434 (2002); Mulligan, C., et al., J. Hazard. Mater., 85: 111-125 (2001). Studies have also shown that the lactone form of sophorolipids has antimicrobial properties (Ashby, R. D., et al., New Biotechnol., 28: 24-30 (2011); Solaiman, D. K. Y., et al., Biocatal. Agric. Biotechnol., 4: 342-348 (2015)) and can be utilized as a bacteriostatic agent (Mager et al. 1987), as spermicides and virucides (Shah, V., et al., Antimicrob. Agents Chemother., 49: 4093-4100 (2005)), as septic shock antagonists (Bluth, M. H., et al., Crit. Care Med., 34: 188-195 (2006); Hardin, R., et al., J. Surg. Res., 142: 314-319 (2007)), as anticancer agents (Chen, J., et al., Enz. Microb. Technol., 39: 501-506 (2006); Fu, S. L., et al., J. Surg. Res., 148: 77-82 (2008)), as stimulant for skin fibroblast metabolism (Borzeix, C., U.S. Pat. No. 6,596,265), and as treatment for skin diseases (Maingault, M., Canadian Patent CAN126242874). In contrast, the acidic form of SLs has been shown to be therapeutically active for skin treatment, particularly as agents for fibrinolysis (promoting healing), desquamation, depigmenting, macrophage activation (Maingault, M., U.S. Pat. No. 5,981,497), and as moisturizing agents (Abe, Y., et al., U.S. Pat. No. 4,297,340; Tsutsumi, H. et al., U.S. Pat. No. 4,305,961). These characteristics have aided in the progress of the industrial utilization of SLs such that they are currently being successfully developed and used in dishwashing detergents by Saraya Co., Ltd. under the trade name Sophoron™, and by Ecover and Soliance for applications in laundry and dishwashing detergents, industrial and institutional cleaners, hand soaps, and cosmeceuticals. In addition, the unique sophorolipid (SL) structure has increased interest in their use as a precursor for the production of specialty chemicals such as sophorose, a known inducer of fungal cellulase enzymes (Sternberg, D., and G. Mandels, J. Bacteriol., 144: 1197-1199 (1980)), monohydroxy fatty acids (Rau, U., et al., Ind. Crop Prod., 13: 85-92 (2001)), and other derivatives (Zerkowski, J., and D. Solaiman, J. Am. Oil Chem. Soc., 83: 621-628 (2006); Zerkowski, J., and D. Solaiman, J. Am. Oil Chem. Soc., 84: 463-471 (2007); Zerkowski, J., et al., J. Am. Oil Chem. Soc., 85: 277-284 (2008)). To a limited extent, structural variation (and hence control over physical properties) can be achieved by changing the hydrophobic carbon source which alters the sophorolipid fatty acid content.

Sugars and sweeteners have an important role in the human diet, and their uses are often determined by their economics and availability, and their suitability in a particular food. Non-caloric sweeteners have been used by consumers for more than 30 years. Although it helped the consumers' need for non-caloric artificial sweeteners, many consumers express interest in additional products, especially products containing natural non-caloric sweeteners. Consumer interest in natural high-potency sweeteners has grown dramatically in recent years, fueled by concerns about the use of artificial additives in foods.

Taste is a sensory response to chemical stimulation of taste receptors by tastants. There are five basic tastes that have been identified: salty, sweet, sour, bitter, and umami. Taste receptor cells are responsible for transducing chemical stimuli from the mouth and relaying information to the nervous system. Sweet stimuli utilize G-protein coupled receptors which activate the phospholipase C (PLC) signaling pathway. The T1R3 receptor subunit acts as a sweet taste receptor in combination with its partner, T1R2. Sweet receptors are activated by a vast repertoire of chemically distinct molecules which specifically interact with certain regions of T1R2+T1R3 sweet receptors (Bachmanov, A. A., and G. K. Beauchamp, Annu. Rev. Nutr., 27: 389-414 (2007); Bachmanov, A. A., et al., Curr. Pharm. Design., 20(16): 2669-83 (2014)).

Sweet is the main attractive taste modality in humans. However, increasing amounts of sugars in food have raised concern about their health effects. The steady increase of the daily consumption of dietary sugar over the last few decades may have contributed to the obesity epidemic and the early onset of type-II diabetes observed in many countries (Malik, V. S., et al., Diabetes Care., 33(11): 2477-8 (2010)). The number of people suffering from diabetes, obesity, hypertension, and heart disease is increasing every year. Today the major goal of diabetes management is control of blood glucose. As an alternative to sugar, which produces calories when it is metabolized in the body, artificial sweeteners are receiving much more attention. However, sugar cannot simply be replaced by intense sweeteners because of the factors of bulk, quality, intensity of sweetness, and physical characteristics. Artificial sweeteners get a bad reputation due to their unwanted/unexpected/nonpleasant taste and the issue of safety. Due to these features of artificial sweeteners, rare sugars are desirable for low calorie as well as bulk sweeteners. These sugars tend to have desirable sweetness but are not metabolized in the human body and therefore do not provide calorie intake. Therefore, there is high demand/ need to have natural sugars with the desired quantities of sweetness, low caloric value, and least observed physiological effects. In addition to plant derived natural sweeteners, next generation natural sweet molecules are produced from microorganisms by using recycled oil and sugar sources. Arabitol, a sugar alcohol which is a stereoisomer to xylitol, produced using *Debaryomyces hansenii*, has the potential application as a sweetener for diabetic patients and reducer of dental caries (Koganti, S., and L.-K. Ju, Biochem. Engineer J., 79: 112-119 (2013)).

Another of the primary taste qualities is bitter, a sensation that arises when specific chemicals are detected by specialized receptors in the tongue. Bitter taste is thought to have evolved as a deterrent against ingesting toxic substances, which may explain why many drugs taste bitter. The T2R family of taste receptors functions as bitter taste receptors (Bachmanov and Beauchamp 2007; Bachmanov et al. 2014). Most T2Rs that have been studied have binding profiles that involve several different bitter-tasting ligands. Many active pharmaceutical ingredients and/or inactive ingredients in medicines and over the counter (OTC) preparations taste bitter and thus are aversive to children as well as many adults (Mennella, J. A., et al., Clin. Ther., 35(8): 1225-46 (2013)). With respect to OTC preparations, such as cough and cold syrups, the bitterness of the preparation leads to lack of patient compliance. Conventional taste masking methods, such as the use of sweeteners, amino acids, and flavoring agents, alone are often inadequate at masking the taste of highly bitter drugs. Another approach is to use bitter blockers, which instead of masking bitter taste by additional flavor eliminate it. It is, therefore, desirable to provide compounds that may be added to food products, consumer products, and pharmaceuticals comprising bitter tastants or having a bitter taste to eliminate, modulate or reduce the perception of the bitter tastants or bitter taste or to reduce the corresponding activation of the bitter receptors (e.g., in the oral cavity and/or the gastrointestinal tract). Similarly, it is desirable to provide food products, consumer products, and pharmaceutical compositions comprising such compounds.

We have found that sophorolipids have both sweet-tasting and bitter-blocking properties.

SUMMARY OF THE INVENTION

Disclosed herein are compounds (e.g., sophorolipids) that modulate bitter taste, edible compositions comprising such compounds, and methods of preparing such edible compositions. The present invention also provides methods of reducing the amount of sugar in an edible composition. The present invention also provides methods of reducing bitter taste of an edible composition. The present invention further provides methods of reducing, modulating or eliminating the bitter taste of a food product, consumer product, or pharmaceutical product in a subject. The present invention also provides methods of modulating, particularly reducing the activation of a bitter taste receptor.

Edible Compositions.

One aspect of the present invention provides edible compositions for reducing bitter taste of a bitter tastant. In some embodiments, the edible composition comprises at least one sophorolipid disclosed herein.

In some embodiments, the edible composition comprises (a) at least one sophorolipid disclosed herein; and (b) a bitter tastant.

According to the invention, the bitter tastant can be inherent in, e.g., a food product (such as coffee or chocolate) or can be a component of an edible composition (such as a bitter tasting preservative). In some embodiments, the bitter tastant present in the edible composition is a bitter tasting salt (e.g., magnesium chloride, calcium chloride and cesium chloride). In some embodiments, the bitter tastant present in the edible composition is a potassium salt, a magnesium salt, or a calcium salt. In some embodiments, the bitter tastant is a potassium salt. In some embodiments, the bitter tastant present in the edible compositions is KCl. In other embodiments, the bitter tastant present in the edible composition is potassium lactate.

In some embodiments, the edible composition further comprises a sodium salt. In some embodiments, the edible composition further comprises NaCl. In other embodiments, the edible composition further comprises sodium lactate. In some embodiments, the edible composition further comprises sugar.

In another aspect of the invention, the edible composition is a food product comprising at least one sophorolipid disclosed herein.

In another aspect of the present invention, the edible composition is a pharmaceutical composition comprising a bitter tasting pharmaceutically active ingredient or inactive ingredient and at least one sophorolipid disclosed herein.

In yet other embodiments, the edible composition is a pharmaceutical composition (e.g., medicine) comprising a pharmaceutically active ingredient, a bitter tastant, and at least one sophorolipid disclosed herein.

In another aspect of the present invention, the edible composition is a consumer product comprising a bitter tastant and at least one sophorolipid disclosed herein.

Yet another embodiment of the present invention provides a consumer product for reducing bitter taste of a bitter tastant, wherein said consumer product comprises at least one sophorolipid disclosed herein.

In a further aspect, the present invention provides a method of preparing an edible composition comprising (a) providing an acceptable carrier (e.g., comestibly acceptable carrier); and (b) adding to the acceptable carrier at least one sophorolipid disclosed herein.

In another embodiment, the method of preparing an edible composition comprises (a) providing a comestibly acceptable carrier; and (b) adding to the comestibly acceptable carrier at least one sophorolipid disclosed herein.

In some embodiments, the edible composition is a food product, a consumer product, or a pharmaceutical composition. In some embodiments, the acceptable carrier (e.g., comestibly acceptable carrier) is a foodstuff, a food product, or a pharmaceutically acceptable carrier.

In some embodiments, the acceptable carrier (e.g., comestibly acceptable carrier) in (a) is inherently bitter. In such embodiments, the acceptable carrier may inherently contain a bitter tastant (i.e., the acceptable carrier is bitter without addition of a bitter tastant). In some embodiments, the inherent bitter tastant is a bitter tasting salt. In some embodiments, the inherently bitter foodstuff comprises a potassium salt, a magnesium salt, or a calcium salt. In some embodiments, the inherently bitter foodstuff comprises a potassium salt, such as KCl.

In other embodiments, the method of preparing an edible composition further comprises (c) adding a bitter tastant. In some embodiments, the bitter tastant used in the methods of preparing an edible composition is a bitter tasting salt. In some embodiments, the bitter tastant used in the methods of preparing an edible composition is a potassium salt, a magnesium salt, or a calcium salt. In some embodiments, the bitter tastant used in the methods of preparing an edible composition is a potassium salt. In some embodiments, the bitter tastant used in the methods of preparing an edible composition is KCl. In other embodiments, the bitter tastant used in the methods of preparing an edible composition is potassium lactate.

In some embodiments, the edible composition further comprises a sodium salt. In some embodiments, the edible composition further comprises NaCl. In some embodiments, the edible composition further comprises sodium lactate (which may taste bitter). In some embodiments, the edible composition further comprises sugar.

The present invention also provides a method of reducing the bitter taste attributed to a bitter tastant in an edible composition comprising adding an effective amount of at least one sophorolipid disclosed herein.

The present invention further provides a method of reducing the bitter taste attributed to a bitter tastant in an edible composition, comprising ingesting an effective amount of at least one sophorolipid disclosed herein, before, along with, or after the edible composition such that any bitter taste induced by the bitter tastant is reduced.

In some embodiments, the edible composition, is a food product, a consumer product or a pharmaceutical composition.

In some embodiments, the method reduces the bitter taste induced by the bitter tastant by up to 25%. In some embodiments, the method reduces the bitter taste induced by the bitter tastant by up to 50%. In other embodiments, the bitter taste induced by the bitter tastant is reduced by up to 75%. In yet other embodiments, the bitter taste induced by the bitter tastant is reduced by up to 100%. In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant present in the edible compositions is KCl.

The present invention also provides a method of reducing or eliminating bitter taste in a subject utilizing an edible composition comprising at least one sophorolipid disclosed herein.

In some embodiments the bitter taste is inherent. In some embodiments, the bitter taste is due to a bitter tasting salt. In some embodiments, the bitter taste is due to a potassium salt, a magnesium salt, or a calcium salt. In some embodiments, the bitter taste is due to KCl. In other embodiments, the bitter taste is due to potassium lactate.

The present invention also provides a method of inhibiting or reducing the activation and/or signaling of a bitter taste receptor (e.g., found on the tongue and body parts, tissues, organs, cells), wherein the method comprises contacting a bitter taste receptor with at least one sophorolipid disclosed herein. In some embodiments, the bitter taste receptor is in the oral cavity. In other embodiments, the bitter taste receptor is in the gastrointestinal tract, for example, in the stomach. In other embodiments, the bitter taste receptor is in an in vitro assay.

In another embodiment, the invention provides a method of reducing the amount of sugar in an edible composition comprising replacing an amount of sugar used in preparing an edible composition with an amount of at least one sophorolipid disclosed herein.

In some embodiments, the edible composition is a food product, a consumer product or a pharmaceutical composition.

In some embodiments of the present invention, the method of reducing the amount of sugar in an edible composition, comprises incorporating into the edible composition an effective amount of at least one sophorolipid disclosed herein sufficient to permit replacement of up to 25% of the sugar present in an edible composition with at least one sophorolipid disclosed herein. In other embodiments, the amount of at least one sophorolipid disclosed herein incorporated into the edible composition is sufficient to permit replacement of up to 50% of the sugar present in an edible composition with at least one sophorolipid disclosed herein. In yet other embodiments, the amount of at least one sophorolipid disclosed herein incorporated into the edible composition is sufficient to permit replacement of up to 75% of the sugar present in an edible composition with at least one sophorolipid disclosed herein. In other embodiments, the amount of at least one sophorolipid disclosed herein incorporated into the edible composition is sufficient to permit replacement of up to 100% of the sugar present in an edible composition with at least one sophorolipid disclosed herein. In some embodiments, the edible composition maintains a sweet flavor. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

The present invention also provides a method of reducing sugar intake of a subject comprising replacing an amount of sugar used in preparing an edible composition with an effective amount of at least one sophorolipid disclosed herein.

In some embodiments, the edible composition is a food product, a consumer product or a pharmaceutical composition.

In some embodiments of the present invention, the methods of reducing the sugar intake of a subject further comprises identifying a subject in need thereof.

In some embodiments, the methods of reducing the sugar intake of a subject comprises incorporating into the edible composition an amount of the sophorolipid sufficient to reduce sugar intake by up to 25% using sophorolipid replacement. In other embodiments, the amount of sophorolipid added is sufficient to reduce sugar intake by up to 50% using sophorolipid replacement. In yet other embodiments, the amount of sophorolipid added is sufficient to reduce sugar intake by up to 75% using sophorolipid replacement. In other embodiments, the amount of sophorolipid added is sufficient to reduce sugar intake by up to 100% using sophorolipid replacement. In some embodiments, the amount of sophorolipid added is sufficient to reduce sugar intake by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the edible composition maintains a sweet flavor. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments of the present invention, the methods of reducing the sugar intake of a subject further comprises identifying a subject in need thereof. In some embodiments, the methods of reducing the sugar intake of a subject comprise incorporating into the edible composition an amount of the sophorolipid sufficient to reduce sugar intake by up to 25% using sophorolipid replacement. In other embodiments, the amount of sophorolipid added is sufficient to reduce sugar intake by up to 50% using sophorolipid replacement. In yet other embodiments, the amount of sophorolipid added is sufficient to reduce sugar intake by up to 75% using sophorolipid replacement. In other embodiments, the amount of sophorolipid added is sufficient to reduce sugar intake by up to 100% using sophorolipid replacement. In yet other embodiments, the amount of sophorolipid added is sufficient to reduce sugar intake by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the edible composition maintains a sweet flavor. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. The sophorolipids disclosed herein also have a role of sweetness enhancers capable of enhancing the sweet taste of sweetener compositions and the sweetener compositions produced therefrom.

Particular embodiments of the invention are set forth in the following paragraphs:

A composition comprising at least one sophorolipid disclosed herein and a carrier; wherein the composition is edible and capable of reducing bitter taste of a bitter tastant.

A composition comprising at least one sophorolipid disclosed herein; and (b) a bitter tastant, wherein the composition is edible. The composition, wherein the bitter tastant is a foodstuff. The composition, wherein the bitter tastant is a bitter tasting salt. The composition, wherein the bitter testing salt is a magnesium salt, a calcium salt, or a potassium salt. The composition, wherein the potassium containing salt is KCl or potassium lactate. The composition, wherein the edible composition further comprises one or more components selected from the group consisting of: NaCl, sodium lactate, and sugar.

A Food Product Comprising the Compositions.

A method of preparing an edible composition comprising (a) providing an acceptable carrier (e.g., comestibly acceptable carrier); and (b) adding to the acceptable carrier at least one sophorolipid disclosed herein. The method, wherein said acceptable carrier is inherently bitter. The method, wherein the acceptable carries comprises a bitter tasting salt. The method, wherein the bitter tasting salt is a magnesium salt, a calcium salt, or a potassium salt. The method, wherein the potassium salt is KCl or potassium lactate. The method, wherein the edible composition further comprises one or more components selected from the group consisting of: NaCl, sodium lactate, and sugar.

The method, wherein the method further comprises (c) adding a bitter tastant. The method, wherein the bitter tastant is a bitter tasting salt. The method, wherein the bitter tasting salt is a magnesium salt, a calcium salt, or a potassium salt. The method, wherein the potassium salt is KCl or potassium lactate. The method, wherein the edible composition further comprises one or more components selected from the group consisting of: NaCl, sodium lactate, and sugar.

A method of reducing bitter taste attributed to a bitter tastant in an edible composition comprising (a) adding an effective amount of at least one sophorolipid disclosed herein to the edible composition such that any bitter taste induced by the bitter tastant is reduced. The method, wherein the edible composition is a food product, a consumer product, or a pharmaceutical composition. The method, wherein the bitter taste induced by the bitter tastant is reduced by up to 25%. The method, wherein the bitter taste induced by the bitter tastant is reduced by up to 50%. The method, wherein the bitter taste induced by the bitter tastant is reduced by up to 75%. The method, wherein the bitter taste induced by the bitter tastant is reduced by up to 100%. In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. The method, wherein the bitter tastant is a bitter tasting salt. The method, wherein the bitter tasting salt is a magnesium salt, a calcium salt, or a potassium salt. The method, wherein the potassium salt is KCl or potassium lactate. The method, wherein the edible composition further comprises NaCl, sodium lactate, or sugar.

A method of reducing bitter taste attributed to a bitter tastant in an edible composition comprising (a) ingesting an effective amount of at least one sophorolipid disclosed herein, along with the edible composition such that any bitter taste induced by the bitter tastant is reduced. The method, wherein the edible composition is a food product, a consumer product, or a pharmaceutical composition. The method, wherein the bitter taste induced by the bitter tastant is reduced by up to 25%. The method, wherein the bitter taste induced by the bitter tastant is reduced by up to 50%. The method, wherein the bitter taste induced by the bitter tastant is reduced by up to 75%. The method, wherein the bitter taste induced by the bitter tastant is reduced by up to 100%. In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. The method, wherein the bitter tastant is a bitter tasting salt. The method, wherein the bitter tasting salt is a magnesium salt, a calcium salt, or a potassium salt. The method, wherein the potassium salt is KCl or potassium lactate. The method, wherein the edible composition further comprises NaCl, sodium lactate, or sugar.

A method of inhibiting, reducing, or eliminating a bitter taste in a subject comprising (a) placing at least one sophorolipid disclosed herein in the oral cavity of the subject. The method, wherein the bitter taste is due to a bitter tasting salt. The method, wherein the bitter taste is due to a magnesium salt, a calcium salt, or a potassium salt. The method, wherein the bitter taste is due to KCl or potassium lactate.

A pharmaceutical composition comprising (a) a bitter tasting pharmaceutical active ingredient or inactive ingredient; and (b) at least one sophorolipid disclosed herein.

A pharmaceutical composition comprising (a) a pharmaceutical active ingredient; (b) a bitter tastant; and (c) at least one sophorolipid disclosed herein.

A consumer product comprising (a) a bitter testing ingredient; and (b) at least one sophorolipid disclosed herein.

A consumer product for reducing bitter taste of a bitter tastant, wherein said consumer product comprises at least one sophorolipid disclosed herein.

A method of inhibiting a bitter taste receptor comprising contacting the bitter taste receptor with at least one sophorolipid disclosed herein. The method, wherein the bitter taste receptor is in the oral cavity of a subject. The method, wherein the bitter taste receptor is in the gastrointestinal tract of a subject. The method, wherein the bitter taste receptor is present in an in vitro assay.

A method of reducing the amount of sugar in an edible composition comprising replacing an amount of sugar used in preparing an edible composition with an effective amount of at least one sophorolipid disclosed herein. The method, wherein the amount of at least one sophorolipid disclosed herein is sufficient to permit replacement of the amount of sugar typically present in the edible composition by up to 25%. The method, wherein the amount of at least one sophorolipid disclosed herein is sufficient to permit replacement of the amount of sugar typically present in the edible composition by up to 50%. The method, wherein the amount of at least one sophorolipid disclosed herein is sufficient to permit replacement of the amount of sugar typically present in the edible composition by up to 75%. The method, wherein the amount of at least one sophorolipid disclosed herein is sufficient to permit replacement of the amount of sugar typically present in the edible composition by up to 100%. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

A method of reducing sugar intake of a subject comprising replacing an amount of sugar used in preparing an edible composition with an amount of at least one sophorolipid disclosed herein, thereby reducing the sugar intake of the subject. The method, wherein the amount of at least one sophorolipid disclosed herein is sufficient to reduce sugar intake by up to 25% by replacement with at least one sophorolipid disclosed herein. The method, wherein the amount of at least one sophorolipid disclosed herein is sufficient to reduce sugar intake by up to 50% by replacement with at least one sophorolipid disclosed herein. The method, wherein the amount of at least one sophorolipid disclosed herein is sufficient to reduce sugar intake by up to 75% by replacement with at least one sophorolipid disclosed herein. The method, wherein the amount of at least one sophorolipid disclosed herein is sufficient to reduce sugar intake by up to 100% by replacement with at least one sophorolipid disclosed herein. In some embodiments, the amount of sugar intake is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

T1R3 alone, possibly as a homodimer, may serve as a low-affinity sweet receptor for carbohydrates. T1R receptors, the taste G protein gustducin, and other taste transduction proteins are expressed in taste cells of the tongue and in a number of non-taste tissues including but not limited to enteroendocrine cells of the gastrointestinal tract and pancreatic islets, and brain. Sugars and artificial sweeteners are powerful agonists of the sweet taste receptors of both tongue and gut and elsewhere. Knockout mice lacking gustducin are deficient in detecting sweet and umami compounds and have dysregulated glucose homeostasis. Yet little attention has been paid to the physiological effects of artificial sweeteners beyond their sweet taste. Of potential relevance is the observation that ingestion of diet soda is associated with an increased risk of metabolic syndrome, thereby increasing the risk for heart disease, stroke, and diabetes (Lutsey, P. L., et al., Circulation, 117: 754-761 (2008)). These studies indicate that taste receptors including T1R3 and other taste signaling proteins expressed in gut and other endocrine organs may have an important role in glucose homeostasis and energy metabolism and that their altered activity may contribute to pathologies such as type II diabetes and obesity. A number of naturally occurring anti-sweet or sweet-modifying substances are suspected to be ligands of the sweet receptor, but to date the site(s) of action of only a few of these compounds have been identified (Kanetkar, P., et al., J. Clin. Biochem. Nutr., 41: 77-81 (2007); Kurihara, Y., Crit. Rev. Food Sci. Nutr., 32: 231-252 (1992)). Compared to activities of agonists of T1R receptors, very little is known of physiological and medicinal roles for sweet and umami receptor antagonists. We also consider SL for future medicine which utilize T1R3 receptors (chemoreceptors associated disorders) located through other part of bodies. We here described novel T1R3 receptor ligand and methods of treatment using the compositions described herein. Conditions, disorders or diseases to be treated with the compositions provided herein include disorders or conditions associated with chemosensory receptors.

In certain embodiments, the methods described herein comprise modulation of hormone concentrations in a subject having a disease or disorder associated with a chemosensory receptor in which the disease or disorder is sadness, stress, grief, anxiety, anxiety disorder (e.g., generalized anxiety disorder, obsessive-compulsive disorder, panic disorder, post-traumatic stress disorder or social anxiety disorder or a mood disorder (e.g., depression, bipolar disorder, dysthymic disorder and cyclothymic disorder). In certain embodiments, the methods comprise methods of inducing feelings of happiness, well-being or contentment in subjects by administering a composition comprising a chemosensory receptor modulator that modulates the concentrations of one or more hormones in a subject.

Additionally, the compositions and methods of the embodiment herein may be used for the dietary management of the conditions associated with a chemosensory receptor listed above. For example, disorders such as frailty, anorexia, cachexia, loss of lean body mass, food associated or food-induced nausea and vomiting, food allergies, and food associated aversive reactions may be treated with chemosensory receptor antagonists.

The compositions described herein can be adapted for release to the upper or small intestine, to the lower or large intestine, or both. For certain indications, the compositions described herein can be adapted for release in the stomach. Administration of the compositions into the intestine is via any known method including oral.

In one aspect, the compositions described herein comprise a bitter receptor ligand selected from absinthine, artemorine, amorogentine, arglabine, azathioprine, azepinone, benzoin, brucine, camphor, cascarillin, chlorhexidine, N,N'-diethylthiourea, herbolide A, isohumulone, noscapine, papaverine, parthenolide, picrotoxinin, arborescine, or (−)-α-thujone, including but not limited to suitable derivatives, wherein the composition is adapted to release a therapeutically effective amount of the ligand to one or more regions of the intestine of a subject. The structural formulae of these compounds are shown below.

In another aspect, the compositions described herein comprise a bitter receptor ligand selected from compounds structurally related to absinthine, arglabine, arborescine, artemorine, noscapine, or parthenolide having the structural Formula I disclosed in US Patent Application No: 2012/0177,730.

BRIEF DESCRIPTION OF THE DRAWINGS

FIG. 6A is for T1R3-KO mice and FIG. 6B is for wild-type B6 mice.

DETAILED DESCRIPTION OF THE INVENTION

Figure 1:
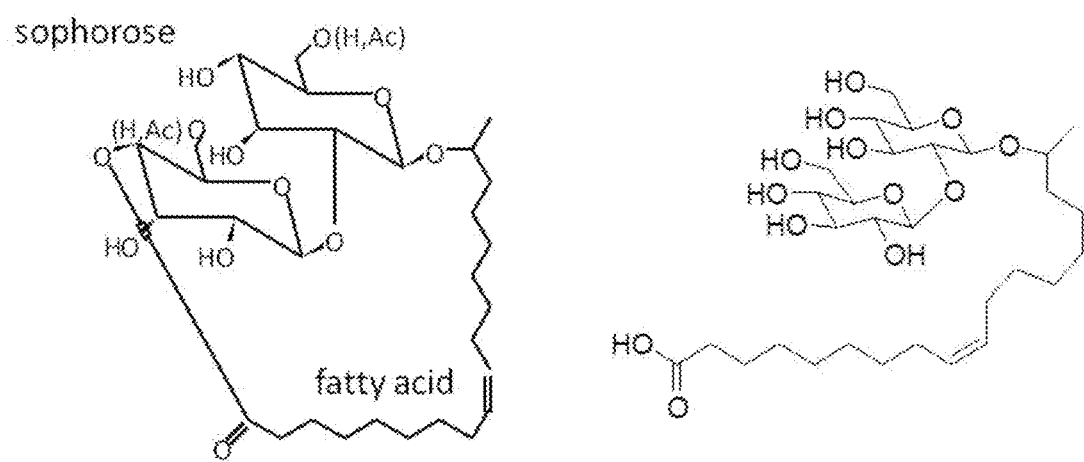
FIG. 1 shows structures of sophorolipids containing 17-hydroxy oleic acid as the lipid moiety are shown in its lactone (left) and free acid (right) form as described below.

Disclosed herein are sophorolipids that modulate bitter taste, edible compositions containing such compounds, and methods of utilizing such edible compositions.

Sophorolipids are molecules composed of a sophorose sugar moiety (2-O-β-D-glucopyranosyl-β-D glucopyranose) and a lipid component. The lipid component may have different chain-length of carbon atoms, preferably C14-C24, more preferably C16-C18. It should be noted that from here on, C16-SL refers to sophorolipids containing 16-carbon chain fatty acid unit and was produced using palmitic acid; C18-SL contains 18-carbon chain fatty acid and was produced using stearic acid; and C18:1-SL contains 18-carbon chain fatty acid having one unsaturated bond and was produced using oleic acid. The sophorolipids may have one or two unsaturated bonds.

The bitter tastant can be inherent in, for example, a food product (such as coffee or chocolate) or can be a component of an edible composition (such as a bitter tasting preservative).

In another aspect of the invention, the edible composition is a food product comprising at least one sophorolipid disclosed herein.

In another aspect of the present invention, the edible composition is a pharmaceutical composition comprising a bitter tasting pharmaceutically active ingredient or inactive ingredient and at least one sophorolipid disclosed herein.

In another embodiment the pharmaceutical composition comprises a bitter tasting pharmaceutically active ingredient or inactive ingredient and at least one sophorolipid disclosed herein.

In yet other embodiments, the edible composition is a pharmaceutical composition comprising a pharmaceutically active ingredient, a bitter tastant, and at least one sophorolipid disclosed herein.

In another aspect of the present invention, the edible composition is a consumer product comprising a bitter tastant and at least one sophorolipid disclosed herein.

In another embodiments, the consumer product comprises a bitter tastant and at least one sophorolipid disclosed herein.

Yet another embodiment of the present invention provides a consumer product for reducing bitter taste of a bitter tastant, wherein said consumer product comprises at least one sophorolipid disclosed herein.

In yet other embodiments, the consumer product for reducing bitter taste of a bitter tastant comprises at least one sophorolipid disclosed herein.

In some embodiments, the edible composition is a food product, a consumer product or a pharmaceutical composition.

The present invention also provides a method of reducing the bitter taste attributed to a bitter tastant in an edible composition, comprising adding an effective amount of at least one sophorolipid disclosed herein to the edible composition such that any bitter taste induced by the bitter tastant is reduced. In some embodiments, the edible composition is a food product, a consumer product, or a pharmaceutical composition.

In some embodiments, the method reduces the bitter taste induced by the bitter tastant by up to 25%. In some embodiments, the method reduces the bitter taste induced by the bitter tastant by up to 50%. In other embodiments, the bitter taste induced by the bitter tastant is reduced by up to 75%. In yet other embodiments, the bitter taste induced by the bitter tastant is reduced by up to 100%. In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

The present invention also provides a method of inhibiting or reducing the activation and/or signaling of a bitter taste receptor, wherein the method comprises contacting a bitter taste receptor with at least one sophorolipid disclosed herein.

In some embodiments, the method inhibits or reduces the activation and/or signaling of a bitter taste receptor by up to 25%. In some embodiments, the method inhibits or reduces the activation and/or signaling of a bitter taste receptor by up to 50%. In other embodiments, the method inhibits or reduces the activation and/or signaling of a bitter taste receptor by up to 75%. In yet other embodiments, the method inhibits or reduces the activation and/or signaling of a bitter taste receptor by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In another embodiment, the invention provides a method of reducing the amount of sugar in an edible composition comprising replacing an amount of sugar used in preparing an edible composition with an amount of at least one sophorolipid disclosed herein.

In some embodiments, the edible composition is a food product, a consumer product or a pharmaceutical composition.

In some embodiments of the present invention, the method of reducing the amount of sugar in an edible composition, comprises incorporating into the edible composition an effective amount of at least one sophorolipid disclosed herein sufficient to permit replacement of up to 25% of the sugar present in an edible composition with at least one sophorolipid disclosed herein. In other embodiments, the amount of at least one sophorolipid disclosed herein incorporated into the edible composition is sufficient to permit replacement of up to 50% of the sugar present in an edible composition with at least one sophorolipid disclosed herein. In yet other embodiments, the amount of at least one sophorolipid disclosed herein incorporated into the edible composition is sufficient to permit replacement of up to 75% of the sugar present in an edible composition with at least one sophorolipid disclosed herein. In other embodiments, the amount of at least one sophorolipid disclosed herein incorporated into the edible composition is sufficient to permit replacement of up to 100% of the sugar present in an edible composition with at least one sophorolipid disclosed herein. In some embodiments, the edible composition maintains a sweet flavor. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

The present invention also provides a method of reducing sugar intake of a subject comprising replacing an amount of sugar used in preparing an edible composition with an effective amount of at least one sophorolipid disclosed herein.

In some embodiments, the edible composition is a food product, a consumer product or a pharmaceutical composition.

In some embodiments of the present invention, the methods of reducing the sugar intake of a subject further comprises identifying a subject in need thereof.

In some embodiments, the methods of reducing the sugar intake of a subject comprises incorporating into the edible composition an amount of the sophorolipid sufficient to reduce sugar intake by up to 25% using sophorolipid replacement. In other embodiments, the amount of sophorolipid added is sufficient to reduce sugar intake by up to 50% using sophorolipid replacement. In yet other embodiments, the amount of sophorolipid added is sufficient to reduce sugar intake by up to 75% using sophorolipid replacement. In other embodiments, the amount of sophorolipid added is sufficient to reduce sugar intake by up to 100% using sophorolipid replacement. In some embodiments, the edible composition maintains a sweet flavor. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments of the present invention, the methods of reducing the sugar intake of a subject further comprises identifying a subject in need thereof. In some embodiments, the methods of reducing the sugar intake of a subject comprise incorporating into the edible composition an amount of the sophorolipid sufficient to reduce sugar intake by up to 25% using sophorolipid replacement. In other embodiments, the amount of sophorolipid added is sufficient to reduce sugar intake by up to 50% using sophorolipid replacement. In yet other embodiments, the amount of sophorolipid added is sufficient to reduce sugar intake by up to 75% using sophorolipid replacement. In other embodiments, the amount of sophorolipid added is sufficient to reduce sugar intake by up to 100% using sophorolipid replacement. In some embodiments, the edible composition maintains a sweet flavor. In some embodiments, the amount of sugar is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

The term "bitter" or "bitter taste" as used herein refers to the perception or gustatory sensation resulting following the detection of a bitter tastant. The following attributes may contribute to bitter taste: astringent, bitter-astringent, metallic, bitter-metallic, as well as off-tastes, aftertastes, and undesirable tastes including but not limited to freezer-burn and cardboard taste, and/or any combinations of these. It is noted that, in the art, the term "off-taste" is often synonymous with "bitter taste." Without being limited by theory, the diversity of bitter tastes may reflect the large number of bitter receptors and the differential detection of bitter tastants by these receptors. Bitter taste as used herein includes activation of a bitter taste receptor by a bitter tastant. Bitter taste as used herein also includes activation of a bitter taste receptor by a bitter tastant followed by downstream signaling. Bitter taste as used herein also includes activation of a signaling pathway after stimulation by a bitter tastant. Bitter taste as used herein further includes perception resulting from signaling following the detection of a bitter tastant by a bitter taste receptor. Bitter taste as used herein further includes perception resulting from signaling following contacting a bitter taste receptor with a bitter tastant. Bitter taste can be perceived in the brain.

The term "bitter taste receptor" refers to a receptor, typically a cell surface receptor, to which a bitter tastant can bind. Bitter taste receptors may be present in the oral cavity, and/or throughout the gastrointestinal tract, including the stomach, intestines, and colon. Bitter receptors can also be present in vitro, such as in an assay, including but not limited to a cell based assay or a binding assay.

The term "bitter tastant," "bitter ligand," or "bitter compound" refers to a compound that activates or that can be detected by a bitter taste receptor and/or confers the perception of a bitter taste in a subject. A "bitter tastant" also refers to a multiplicity of compounds that combine to activate or be detected by a bitter taste receptor and/or confer the perception of a bitter taste in a subject. A "bitter tastant" further refers to a compound that is enzymatically modified upon ingestion by a subject to activate or be detected by a bitter taste receptor and/or confer the perception of a bitter taste in a subject. Because the perception of bitter taste may vary from individual to individual, some individuals may describe a "bitter tastant" as a compound which confers a different kind of bitter taste compared to the kind of bitter taste perceived for the same compound by other individuals. The term bitter tastant also refers to a compound which confers a bitter taste. Those of skill in the art can readily identify and understand what is meant by a bitter tastant. Non-limiting examples of bitter tastants or substances including foods that comprise a bitter tastant and taste bitter including coffee, unsweetened cocoa, marmalade, bitter melon, beer, bitters, citrus peel, dandelion greens, escarole, quinine, magnesium salts, calcium salts, potassium salts, KCl, potassium lactate, Acesulfame K, Brussels sprouts, asparagus, bitter gourd, wild cucumber, celery, hops, kohlrabi, radish leaf, *ginseng*, pumpkin, collard greens, kale, sparteine, caffeine, atropine, nicotine, urea and strychnine.

Further examples of bitter tastants include pharmaceuticals Non-limiting examples of pharmaceuticals as bitter tastants include acetaminophen, ampicillin, azithromycin, chlorpheniramine, cimetidine, dextromethorphan, diphenhydramine, erythromycin, ibuprofen, penicillin, phenylbutazone, pseudoephedrine, ranitidine, spironolactone and theophylline all of which have been associated with bitter taste.

The term "consumer product" refers to health and beauty products for the personal use and/or consumption by a subject. Consumer products may be present in any form including, but not limited to, liquids, solids, semi-solids, tablets, capsules, lozenges, strips, powders, gels, gums, pastes, slurries, syrups, aerosols and sprays. Non-limiting examples of consumer products include nutraceuticals, nutritional supplements, lipsticks, lip balms, soaps, shampoos, gums, adhesives (e.g., dental adhesives), toothpastes, oral analgesics, breath fresheners, mouthwashes, tooth whiteners, and other dentifrices.

The term "diet" collectively refers to the food products and/or beverages consumed by a subject. A subject's "diet" also includes any consumer products or pharmaceutical compositions the subject ingests.

The term "edible composition" refers to a composition suitable for consumption, typically via the oral cavity (although consumption may occur via non-oral means such as inhalation). Edible compositions may be present in any form including, but not limited to, liquids, solids, semi-solids, tablets, lozenges, powders, gels, gums, pastes, slurries, syrups, aerosols and sprays. As used herein, edible compositions include food products, pharmaceutical compositions, and consumer products. The term edible compositions also refers to, for example, dietary and nutritional supplements. As used herein, edible compositions also include compositions that are placed within the oral cavity but not swallowed, including professional dental products, such as dental, treatments, fillings, packing materials, molds and polishes. The term "comestible" refers to similar compositions and is generally used as a synonym to the term "edible."

The term "effective amount" refers to an amount sufficient to produce a desired property or result. For example, an effective amount of a compound of the present invention is an amount capable of reducing the perception of bitter taste associated with a bitter tastant. The term "effective amount" also refers to the amount of a compound of the present invention capable of reducing or eliminating the perception of a bitter taste or aftertaste associated with either a bitter tastant in a food product or an inherently bitter food product. As will be pointed out below, the exact amount required will vary. Thus, it is not possible to specify an exact "effective amount." However, an appropriate effective amount may be determined by one of ordinary skill in the art using only routine experimentation.

The term "flavor modifier" refers to a compound or a mixture of compounds that, when added to an edible composition, such as a food product, modifies (e.g., masks, eliminates, decreases, reduces, or enhances the perception of) a flavor (e.g., sweet, salty, umami, sour, or bitter taste) present in the edible composition.

The term "food product" refers to any composition comprising one or more processed foodstuff. Food products include, but are not limited to, confectioneries, bakery products (including, but not limited to, doughs, breads, biscuits, crackers, cakes, pastries, pies, tarts, quiches, and cookies), ice creams (including but not limited to impulse ice cream, take-home ice cream, frozen yogurt, gelato, sorbet, sherbet and soy, oat, bean and rice-based ice cream), dairy products (including, but not limited to, drinking milk, cheese, yogurt, and sour milk drinks), cheeses (including, but not limited to, natural cheeses and processed cheeses), butter, margarine, sweet and savory snacks (including but not limited to fruit snacks, chips/crisps, tortilla/corn chips, popcorn, pretzels, chocolates, and nuts), hot and cold beverages (including, but not limited to, beverages, beverage mixes, concentrates, juices, carbonated beverages, non-carbonated beverages, alcoholic beverages, non-alcoholic beverages, soft drinks, sports drinks, isotonic drinks, coffees, teas, bottled waters, and beverages prepared from botanicals and botanical extracts (including cold beverages that are prepared with botanical or fungi extracts as ingredients, and drinks that are prepared in various ways, such as infusions, decoctions, or other means of extraction or distillation of various plant parts, including, but not limited to leaves, flowers, stems, fruits, roots, rhizomes, stems, bark, volatile oils, or even the whole plant)), snack bars (including, but not limited to granola bars, muesli bars, protein bars, breakfast bars, energy bars, and fruit bars), meal replacement products, ready meals (including, but not limited to canned meals, preserved meals, frozen meals, dried meals, chilled meals, dinner mixes, frozen pizza, chilled pizza, and prepared salads), soups (including but not limited to broth-like soups and cream-based soups), broth, gravy, soy sauce, meats and fish (including raw, cooked, and dried meats), deli products (including but not limited to meats and cheeses suitable for slicing or pre-sliced meats and cheeses, e.g., turkey, chicken, ham, bologna, salami, bierwurst, capicola, chorizo, corned beef, dutch loaf, Serrano, prosciutto, head cheese, liverwurst, meatloaf (including olive loaf, pepper loaf, pimento loaf, and ham and cheese loaf), mortadella, pastrami, pepperoni, roast beef, roast pork, saucisson, smoked meat, summer sausage, tongue, American cheese, blue cheese, cheddar cheese, Colby cheese, Colby-Jack cheese, gouda, Monterey Jack cheese, muenster cheese mozzarella, parmigiano cheese, pepper jack cheese, provolone, romano cheese, string cheese, spray cheese, and swiss cheese), vegetables (including, but not limited to, raw, pickled, cooked, and dried vegetables, such as french fries), fruits (including raw, cooked, and dried fruits), grains (including, but not limited to, dried cereals and breads), prepared foods (including, but not limited to, dried, canned, or jarred sauces and soups), snack foods, pastes (including, but not limited to, fresh pasta, chilled pasta, frozen paste, dried pasta), noodles (including, but not limited to, egg noodles, wheat noodles, rice noodles, mung bean noodles, potato noodles, buckwheat noodles, corn noodles, cellophane noodles, chow mein, fettuccini, fusilli, gnocchi, lasagna, linguini, lo mein, macaroni, manicotti, pad thai, penne, ramen, rice vermicelli, rigatoni, soba, spaghetti, spatzle, udon, and ziti), canned foods, frozen foods, dried foods, chilled foods, oils and fats, baby food, spreads, salads, cereals (including, but not limited to, hot and cold cereals), sauces (including, but not limited to, tomato pastes, tomato purees, bouillon cubes, stock cubes, table sauces, boys bases sauces, pasta sauces, cooking sauces, marinades, dry sauces, powder mixes, ketchups, mayonnaises, salad dressings, vinegrettes, mustards, and dips), jellies, jams, preserves, honey, puddings, recipe mixes, syrups, icings, fillings, infused foods, salt-preserved food, marinated foods and condiments (such as ketchup, mustard and steak sauce). In some embodiments, the food product is animal feed. For example, the food product may be a pet food product, i.e. a food product for consumption by a household pet. In other embodiments, the food product is a livestock food product, i.e. a food product for consumption by livestock.

The term "foodstuff" refers to an unprocessed ingredient or a basic nutrient or flavor containing element used to prepare a food product. Non-limiting examples of foodstuffs include fruits, vegetables, meats, fishes, grains, milks, eggs, tubers, sugars, sweeteners, oils, herbs, snacks, sauces, spices and salts.

The terms "perception of a bitter taste," "perception of saltiness," "perception of a flavor" and similar terms, refer to the awareness of a subject of a particular taste or flavor.

The term "pharmaceutically active ingredient" refers to a compound in a pharmaceutical composition which is biologically active.

The term "processed foodstuff" refers to a foodstuff has been subjected to any process which alters its original state (excluding, e.g., harvesting, slaughtering, and cleaning). Examples of methods of processing foods include, but are not limited to, removal of unwanted outer layers, such as potato peeling or the skinning of peaches; chopping or slicing; mincing or macerating; liquefaction, such as to produce fruit juice; fermentation (e.g. beer); emulsification; cooking, such as boiling, broiling, frying, heating, steaming or grilling; deep frying; baking; mixing; addition of gas such as air entrainment for bread or gasification of soft drinks; proofing; seasoning (with, e.g., herbs, spices, salts); spray drying; pasteurization; packaging (e.g., canning or boxing); extrusion; puffing; blending; and preservation (e.g., adding salt, sugar, potassium lactate or other preservatives).

The term "subject" refers to a mammal. In preferred embodiments, the subject is human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include alpaca, bison, camel, cattle, deer, pigs, horses, llamas, mules, donkeys, sheep, goats, rabbits, reindeer, and yak.

The term "carrier" may be, for example, agronomically or physiologically or pharmaceutically or comestibly acceptable carriers or carrier material known in the art.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

Unless defined otherwise, all technical and scientific terms used herein have the same meaning as commonly understood by one of ordinary skill in the art to which the invention belongs. As used herein, the term "about" refers to a quantity, level, value or amount that varies by as much as 10% to a reference quantity, level, value or amount. Although any methods and materials similar or equivalent to those described herein can be used in the practice or testing of the present invention, the preferred methods and materials are now described.

The present invention provides edible compositions comprising at least one sophorolipid disclosed herein, including food products, consumer products, and pharmaceutical compositions comprising said sophorolipids, and methods of preparing such compositions.

Edible Compositions:

According to one aspect, the invention provides an edible composition comprising at least one sophorolipid disclosed herein for reducing bitter taste of a bitter tastant.

In some embodiments, the bitter tastant present, in the edible composition, is a bitter testing salt. In some embodiments, the bitter tastant present, in the edible composition is a potassium salt, a magnesium salt, or a calcium salt. In some embodiments, the bitter tastant present in the edible composition is a potassium salt. In some embodiments, the bitter tastant present in the edible compositions is KCl. In other embodiments, the bitter tastant present in the edible composition is potassium lactate.

In another embodiment, the edible compositions comprise (a) at least one sophorolipid disclosed herein; and (b) a potassium salt. In some embodiments, the potassium salt is KCl or potassium lactate. In specific embodiments, the potassium salt is KCl.

In some embodiments, the edible composition further comprises a sodium salt. In some embodiments, the edible compositions further comprise NaCl. In some embodiments, the edible compositions further comprise sodium lactate. In some embodiments, the edible compositions further comprise sugar.

In some embodiments, the edible composition further comprises one or more additional components selected from the group consisting of preservatives, nutritives, flavorants or additional flavor modifiers, which may lack an inherent flavor.

In some embodiments, the edible composition further comprises one or more emulsifiers. Sodium and potassium based emulsifiers are commonly used as emulsifiers in the food art. Sodium-based emulsifiers include, e.g., sodium salts of fatty acids, sodium alginate, sodium aluminum phosphate, sodium caseinate, sodium metaphosphate, sodium phosphate (dibasic), sodium phosphate (monobasic), sodium phosphate (tribasic), sodium polyphosphate, sodium pyrophosphate, and sodium stearoyl lactylate. Potassium-based emulsifiers include, e.g., potassium salts of fatty acids, potassium alginate, potassium citrate, potassium phosphate (dibasic), potassium phosphate (monobasic), potassium phosphate (tribasic), potassium polyphosphate, potassium polymetaphosphate, and potassium pyrophosphate. Accordingly, some embodiments of the present invention include replacing a sodium-based emulsifier with a potassium-based emulsifier and adding at least one sophorolipid disclosed herein.

In some embodiments, the edible composition further comprises a surfactant to increase or decrease the effectiveness of the sophorolipid. Suitable surfactants include, but are not limited to, non-ionic surfactants (e.g., mono and diglycerides, fatty acid esters, sorbitan esters, propylene glycol esters, and lactylate esters), anionic surfactants (e.g., sulfosuccinates and lecithin), and cationic surfactants (e.g., quaternary ammonium salts).

In some embodiments wherein the edible compositions further comprises a preservative, the preservative improves the shelf life of the edible composition. Suitable preservatives include, but are not limited to, ascorbic acid, benzoic acid, butyl p-hydroxybenzoate, calcium benzoate, calcium disodium EDTA, calcium hydrogen sulfite, calcium propionate, calcium sorbate, chitosan, cupric sulfate, dehydroacetic acid, diethyl pyrocarbonate, dimethyl dicarbonate, disodium EDTA, E-polylysine glycine, erythorbic acid, ethyl p-hydroxybenzoate, formic acid, gum guaiac, heptylparaben, hinokitiol, isobutyl paraoxybenzoate, Japanese styrax benzoin extract, methylparaben, milt protein extract, natamycin, nisin, peptin extract, 2-phenylphenol, pimaricin, potassium acetate, potassium benzoate, potassium lactate, potassium metabisulfite, potassium nitrate, potassium nitrite, potassium pyrosulfite, potassium sorbate, potassium sulfite, propionic acid, propyl p-hydroxybenzoate, propyl p-oxybenzoate, propylene oxide, propylparaben, sodium benzoate, sodium bisulfite, sodium dehydroacetate, sodium diacetate, sodium erythorbate, sodium hydrogen sulfite, sodium hypophosphite, sodium hyposulfite, sodium metabisulfite, sodium nitrate, sodium nitrite, sodium o-phenylphenol, sodium propionate, sodium pyrosulfite, sodium sulfite, sodium thiocyanate, sorbic acid and sulfur dioxide. In some embodiments, the preservative has a bitter flavor.

In some embodiments, the composition may further comprise one or more additional components selected from, the group consisting of flow agents, processing agents, sugars, amino acids, other nucleotides, and sodium or potassium salts of organic acids such as citrate and tartarate. Such additional ingredients may add flavor, or aid in blending, processing or flow properties of the edible composition.

In some embodiments, the rate of release of the sophorolipid is regulated. The release rate of the sophorolipid can be altered by, for example, varying its solubility in water. Rapid release can be achieved by encapsulating the sophorolipid with a material with high water solubility. Delayed release of the sophorolipid can be achieved by encapsulating the sophorolipid with a material with low water solubility. The sophorolipid can be co-encapsulated with carbohydrates or masking tastants such as sweeteners. The rate of release of the sophorolipid can also be regulated by the degree of encapsulation. In some embodiments, the sophorolipid is fully encapsulated. In other embodiments, the sophorolipids are partially encapsulated. In some embodiments, the rate of release is regulated so as to release with the bitter tastant.

The edible compositions of this invention are prepared according to techniques well-known in the art. In general, an edible composition of the invention is prepared by mixing a component or ingredient of the edible composition with at least one sophorolipid. Alternatively, sophorolipids can be added directly to the edible composition. In some embodiments, a bitter tastant is added simultaneously or sequentially with the sophorolipids. If sequentially, the bitter tastant may be added before or after the sophorolipids. In some embodiments, the edible composition is a food product. In some embodiments, the edible composition is a pharmaceutical composition. In some embodiments, the edible composition is a consumer product.

The amount of both the sophorolipids and a bitter tastant used in an edible composition depends upon a variety of factors, including the purpose of the composition and the desired or acceptable perception of bitterness, saltiness, or sweetness. The amount may depend on the nature of the edible composition, the particular sophorolipid added, the bitter tastant, other compounds present in the composition, the method of preparation (including amount of heat used), and the pH of the edible composition. It will be understood that those of skill in the art will know how to determine the amounts needed to produce the desired taste(s).

In general, a sophorolipid in an edible composition may be present at a concentration between about 0.001 ppm and 1000 ppm. In some embodiments, the edible composition comprises between about 0.005 to 500 ppm; 0.01 to 100 ppm; 0.05 to 50 ppm; 0.1 to 5 ppm; 0.1 to 10 ppm; 1 to 10 ppm; 1 to 30 ppm; 1 to 50 ppm; 10 to 30 ppm; 10 to 50 ppm; or 30 to 50 ppm of the sophorolipid. In yet other embodiments, the edible composition comprises about 0.1 to 30 ppm, 1 to 30 ppm or 1 to 50 ppm of the sophorolipid. In additional embodiments, the edible composition comprises about 0.1 to 5 ppm; 0.1 to 4 ppm; 0.1 to 3 ppm; 0.1 to 2 ppm; 0.1 to 1 ppm; 0.5 to 5 ppm; 0.5 to 4 ppm; 0.5 to 3 ppm; 0.5 to 2 ppm; 0.5 to 1.5 ppm; 0.5 to 1 ppm; 5 to 15 ppm; 6 to 14 ppm; 7 to 13 ppm; 8 to 12 ppm; 9 to 11 ppm; 25 to 35 ppm; 26 to 34 ppm; 27 to 33 ppm; 28 to 32 ppm; or 29 to 31 ppm. In yet other embodiments, the edible composition comprises about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, or about 10 ppm of the sophorolipid. In other embodiments, the edible composition comprises about 11 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, or about 30 ppm of the sophorolipid. In still other embodiments, the edible composition comprises about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, or about 50 ppm of the sophorolipid. In other embodiments, the edible composition comprises more than about 0.5 ppm, 1 ppm, 5 ppm, 10 ppm, 15 ppm, 20 ppm, 25 ppm, or 30 ppm of the sophorolipid, up to, for example, about 30 ppm or 50 ppm. In additional embodiments, the edible composition comprises less than about 50 ppm, 30 ppm, 25 ppm, 20 ppm, 15 ppm, 10 ppm, 5 ppm, 1 ppm, or 0.5 ppm of the sophorolipid. In yet additional embodiments, the edible composition comprises less than about 30 ppm, 10 ppm, or 1 ppm of the sophorolipid. These amounts (ppm) are not meant to be limiting, and increments between the recited percentages are specifically envisioned as part of the invention.

In some embodiments, the edible compositions are included in a package. In some embodiments, the edible composition is packaged in bulk in which the package contains more of the compositions than would typically be used for a single dish or serving of food or beverage. Such bulk packages can be in the form of paper, plastic, or cloth bags or cardboard boxes or drums. Such bulk packages may be fitted with plastic or metal spouts to facilitate the dispensing of the edible composition.

In some embodiments, the package contains an edible composition comprising the sophorolipid and a bitter tastant. In some embodiments, the package contains an edible composition comprising a sophorolipid and bitter tasting salt. In some embodiments, the package contains an edible composition comprising a sophorolipid and a potassium salt, a magnesium salt, or a calcium salt. In some embodiments, the package contains an edible composition comprising a sophorolipid and a potassium salt. In some embodiments, the package contains an edible composition comprising a sophorolipid and KCl. In other embodiments, the package contains an edible composition comprising a sophorolipid and potassium lactate. In some embodiments, the package contains an edible composition comprising a sophorolipid a potassium salt, and a sodium salt. In other embodiments, the package contains an edible composition comprising a sophorolipid, KCl and NaCl. In yet other embodiments, the package contains an edible composition comprising a sophorolipid, potassium lactate and sodium lactate. In other embodiments, the package contains an edible composition comprising a sophorolipid and Acesulfame K and sugar. In other embodiments, the package contains an edible composition comprising a sophorolipid, potassium lactate, KCl and NaCl.

In some embodiments, the edible compositions of the present invention are compositions suitable to be used as seasonings, as ingredients in food products, or as condiments. In such embodiments, the edible composition may or may not contain a bitter tastant. For example, the edible composition may be used in, e.g., a seasoning which comprises a bitter tastant such as, e.g., KCl. Such seasonings can be used in the place of table salt (i.e., NaCl) to season prepared food products. Alternatively, the edible composition may be used in, e.g., a seasoning which does not contain a bitter tastant. Such seasonings can be used to season prepared food products which contain a bitter tastant (either inherently present or added during preparation) in order to reduce the bitter taste associated with the bitter tastant. In some embodiments, the edible composition is a seasoning comprising KCl and a sophorolipid. In some embodiments, the edible composition is a seasoning comprising KCl, NaCl and a sophorolipid. In some embodiments the seasoning further comprises a spice or a blend of spices.

Alternatively, the edible compositions may be used for medicinal or hygienic purposes, for example, in soaps, shampoos, mouthwash, medicines, pharmaceuticals, cough syrup, nasal sprays, toothpaste, dental adhesives, tooth whiteners, glues (e.g., on stamps and envelopes), and toxins used in insect and rodent control.

Food Product:

In some embodiments, the edible composition is a food product. According to such embodiments, the food product comprises (a) a food stuff; and (b) at least one sophorolipid disclosed herein.

In some embodiments, the food product further comprises a bitter tastant, as described herein. In some embodiments, the bitter tastant is a potassium salt, such as KCl or potassium lactate. In specific embodiments, the potassium salt is KCl.

In some embodiments, the food product further comprises one or more additional flavor modifiers.

In some embodiments, the food product further comprises one or more additional components selected from the group consisting of preservatives, nutritives, flavorants or additional flavor modifiers, which may lack an inherent flavor.

In general, a sophorolipid in a food product may be present at a concentration between about 0.001 ppm and 1000 ppm. In some embodiments, the food product comprises between about 0.005 to 500 ppm; 0.01 to 100 ppm; 0.05 to 50 ppm; 0.1 to 5 ppm; 0.1 to 10 ppm; 1 to 10 ppm; 1 to 30 ppm; 1 to 50 ppm; 10 to 30 ppm; 10 to 50 ppm; or 30 to 50 ppm of the sophorolipid. In yet other embodiments, the food product comprises about 0.1 to 30 ppm, 1 to 30 ppm or 1 to 50 ppm of the sophorolipid. In additional embodiments, the food product comprises about 0.1 to 5 ppm; 0.1 to 4 ppm; 0.1 to 3 ppm; 0.1 to 2 ppm; 0.1 to 1 ppm; 0.5 to 5 ppm; 0.5 to 4 ppm; 0.5 to 3 ppm; 0.5 to 2 ppm; 0.5 to 1.5 ppm; 0.5 to 1 ppm; 5 to 15 ppm; 6 to 14 ppm; 7 to 13 ppm; 8 to 12 ppm; 9 to 11 ppm; 25 to 35 ppm; 26 to 34 ppm; 27 to 33 ppm; 28 to 32 ppm; or 29 to 31 ppm. In yet other embodiments, the food product comprises about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, or about 10 ppm of the sophorolipid. In other embodiments, the food product comprises about 11 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, or about 30 ppm of the sophorolipid. In still other embodiments, the food product comprises about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, or about 50 ppm of the sophorolipid. In other embodiments, the food product comprises more than about 0.5 ppm, 1 ppm, 5 ppm, 10 ppm, 15 ppm, 20 ppm, 25 ppm, or 30 ppm of the sophorolipid, up to, for example, about 30 ppm or 50 ppm. In additional embodiments, the food product comprises less than about 50 ppm, 30 ppm, 25 ppm, 20 ppm, 15 ppm, 10 ppm, 5 ppm, 1 ppm, or 0.5 ppm of the sophorolipid. In yet additional embodiments, the food product comprises less than about 30 ppm, 10 ppm, or 1 ppm of the sophorolipid. These amounts (ppm) are not meant to be limiting, and increments between the recited percentages are specifically envisioned as part of the invention.

Pharmaceutical Composition:

In some embodiments, the edible composition is a pharmaceutical composition. According to such embodiments, the pharmaceutical composition, comprises (a) a bitter tasting pharmaceutically active ingredient and/or inactive ingredient; and (b) at least one sophorolipid disclosed herein.

According to some embodiments, the pharmaceutical composition can comprise any bitter tasting pharmaceutically active ingredient and/or inactive ingredient. Non-limiting examples of bitter pharmaceutical compounds include: acetaminophen, ampicillin, azithromycin, chlorpheniramine, cimetidine, dextromethorphan, diphenhydramine, erythromycin, ibuprofen, penicillin, phenylbutazone, pseudoephedrine, ranitidine, spironolactone statins (including, but not limited to, atorvastatin, cerivastatin, fluvastatin, louvastatin, mevastatin, pravastatin, pravastatin, rosuvastatin, and simvastatin) and theophylline.

In other embodiments, the invention provides a pharmaceutical composition comprising (a) a pharmaceutically active ingredient; (b) at least one sophorolipid disclosed herein; and (c) a bitter tastant. In such embodiments, the pharmaceutical compositions may comprise any pharmaceutically active ingredient.

In other embodiments, the invention provides a pharmaceutical composition comprising (a) a pharmaceutically active ingredient; (b) at least one sophorolipid disclosed herein; and (c) a potassium salt. In some embodiments, the potassium salt is KCl or potassium lactate. In some embodiments, the potassium salt is KCl.

In some embodiments, the pharmaceutical composition further comprises one or more additional flavor modifiers.

In some embodiments, the pharmaceutical composition further comprises one or more additional components selected from the group consisting of preservatives, nutritives, flavorants or flavor modifiers, which may lack an inherent flavor.

In general, a sophorolipid in a pharmaceutical composition may be present at a concentration between about 0.001 ppm and 1000 ppm. In some embodiments, the pharmaceutical composition comprises between about 0.005 to 500 ppm; 0.01 to 100 ppm; 0.05 to 50 ppm; 0.1 to 5 ppm; 0.1 to 10 ppm; 1 to 10 ppm; 1 to 30 ppm; 1 to 50 ppm; 10 to 30 ppm; 10 to 50 ppm; or 30 to 50 ppm of the sophorolipid. In yet other embodiments, the pharmaceutical composition comprises about 0.1 to 30 ppm, 1 to 30 ppm or 1 to 50 ppm of the sophorolipid. In additional embodiments, the pharmaceutical composition comprises about 0.1 to 5 ppm; 0.1 to 4 ppm; 0.1 to 3 ppm; 0.1 to 2 ppm; 0.1 to 1 ppm; 0.5 to 5 ppm; 0.5 to 4 ppm; 0.5 to 3 ppm; 0.5 to 2 ppm; 0.5 to 1.5 ppm; 0.5 to 1 ppm; 5 to 15 ppm; 6 to 14 ppm; 7 to 13 ppm; 8 to 12 ppm; 9 to 11 ppm; 25 to 35 ppm; 26 to 34 ppm; 27 to 33 ppm; 28 to 32 ppm; or 29 to 31 ppm. In yet other embodiments, the pharmaceutical composition comprises about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, or about 10 ppm of the sophorolipid. In other embodiments, the pharmaceutical composition comprises about 11 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, or about 30 ppm of the sophorolipid. In still other embodiments, the pharmaceutical composition comprises about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, or about 50 ppm of the sophorolipid. In other embodiments, the pharmaceutical composition comprises more than about 0.5 ppm, 1 ppm, 5 ppm, 10 ppm, 15 ppm, 20 ppm, 25 ppm, or 30 ppm of the sophorolipid, up to, for example, about 30 ppm or 50 ppm. In additional embodiments, the pharmaceutical composition comprises less than about 50 ppm, 30 ppm, 25 ppm, 20 ppm, 15 ppm, 10 ppm, 5 ppm, 1 ppm, or 0.5 ppm of the sophorolipid. In yet additional embodiments, the pharmaceutical composition comprises less than about 30 ppm, 10 ppm, or 1 ppm of the sophorolipid. These amounts (ppm) are not meant to be limiting, and increments between the recited percentages are specifically envisioned as part of the invention.

Consumer Product:

In some embodiments, the edible compositions is a consumer product. According to such embodiments, the consumer product comprises (a) a bitter tastant; and (b) at least one sophorolipid disclosed herein.

In another embodiment, the invention provides a consumer product comprising (a) a potassium salt; and (b) at least one sophorolipid disclosed herein. In some embodiments, the potassium salt is KCl or potassium lactate. In some embodiments, the potassium salt is KCl.

In other embodiments, the invention provides a consumer product for reducing bitter taste of a bitter tastant, wherein said consumer product comprises at least one sophorolipid disclosed herein. In some embodiments, the bitter tastant is a potassium salt. In some embodiments, the potassium salt, is KCl or potassium lactate. In some embodiments, the bitter tastant is KCl.

In some embodiments, the consumer product further comprises one or more additional flavor modifiers.

In some embodiments, the consumer product further comprises one or more additional components selected from the group consisting of preservatives, nutritives, flavorants or additional flavor modifiers, which may lack an inherent flavor.

In general, a sophorolipid in a consumer product may be present at a concentration between about 0.001 ppm and 1000 ppm. In some embodiments, the consumer product comprises between about 0.005 to 500 ppm; 0.01 to 100 ppm; 0.05 to 50 ppm; 0.1 to 5 ppm; 0.1 to 10 ppm; 1 to 10 ppm; 1 to 30 ppm; 1 to 50 ppm; 10 to 30 ppm; 10 to 50 ppm; or 30 to 50 ppm of the sophorolipid. In yet other embodiments, the consumer product comprises about 0.1 to 30 ppm, 1 to 30 ppm or 1 to 50 ppm of the sophorolipid. In additional embodiments, the consumer product comprises about 0.1 to 5 ppm; 0.1 to 4 ppm; 0.1 to 3 ppm; 0.1 to 2 ppm; 0.1 to 1 ppm; 0.5 to 5 ppm; 0.5 to 4 ppm; 0.5 to 3 ppm; 0.5 to 2 ppm; 0.5 to 1.5 ppm; 0.5 to 1 ppm; 5 to 15 ppm; 6 to 14 ppm; 7 to 13 ppm; 8 to 12 ppm; 9 to 11 ppm; 25 to 35 ppm; 26 to 34 ppm; 27 to 33 ppm; 28 to 32 ppm; or 29 to 31 ppm. In yet other embodiments, the consumer product comprises about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, or about 10 ppm of the sophorolipid. In other embodiments, the consumer product comprises about 11 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, or about 30 ppm of the sophorolipid. In still other embodiments, the consumer product comprises about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, or about 50 ppm of the sophorolipid. In other embodiments, the consumer product comprises more than about 0.5 ppm, 1 ppm, 5 ppm, 10 ppm, 15 ppm, 20 ppm, 25 ppm, or 30 ppm of the sophorolipid, up to, for example, about 30 ppm or 50 ppm. In additional embodiments, the consumer product comprises less than about 50 ppm, 30 ppm, 25 ppm, 20 ppm, 15 ppm, 10 ppm, 5 ppm, 1 ppm, or 0.5 ppm of the sophorolipid. In yet additional embodiments, the consumer product comprises less than about 30 ppm, 10 ppm, or 1 ppm of the sophorolipid. These amounts (ppm) are not meant to be limiting, and increments between the recited percentages are specifically envisioned as part of the invention.

Method of Preparing an Edible Composition:

According to another aspect, the invention provides a method of preparing an edible composition. The method comprises: (a) providing an acceptable carrier (e.g., comestibly acceptable carrier); and (b) adding to the acceptable carrier at least one sophorolipid disclosed herein. In some embodiments, the compound of the invention has been dissolved in a solvent prior to the addition step (b).

In some embodiments, the acceptable carrier (e.g., comestibly acceptable carrier) in (a) is inherently bitter. In such embodiments, the acceptable carrier may inherently contain a bitter tastant. In some embodiments, the inherent bitter tastant is a bitter tasting salt. In some embodiments, the inherent, bitter tastant is a potassium salt, a magnesium salt, or a calcium salt. In some embodiments, the inherent bitter tastant is a potassium salt. In some embodiments, the inherent bitter tastant is KCl. In other embodiments, the inherent bitter tastant is potassium lactate.

In some embodiments, the method of preparing an edible composition further comprises: (c) adding a bitter tastant. In some embodiments, the bitter tastant is a potassium salt. In some embodiments, the potassium salt is KCl or potassium lactate. In specific embodiments, the potassium salt is KCl. In some embodiments, the bitter tastant is added before the sophorolipid. In other embodiments, the bitter tastant is added after the sophorolipid. In some embodiments, the sophorolipids are combined with the bitter tastant and then combined with the comestibly acceptable carrier. In other embodiments, the sophorolipid is combined sequentially with the comestibly acceptable carrier and then the bitter tastant. In yet other embodiments, the sophorolipids are combined with a mixture of the bitter tastant and the comestibly acceptable carrier.

In some embodiments, the sophorolipids and the bitter tastant, if present, are mixed with the acceptable carrier (e.g., comestibly acceptable carrier). In other embodiments, the sophorolipids and the bitter tastant, if present, are sprayed onto or coat the acceptable carrier. In some embodiments, the sophorolipid is plated on a carbohydrate or salt, encapsulated on a salt or a carbohydrate (spray dried), or co-crystallized with a potassium salt to create a "topping" salt.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the edible composition further comprises a sodium salt. In some embodiments, the edible composition further comprises NaCl. In other embodiments, the edible composition further comprises sodium lactate. In further embodiments, the edible composition further comprises sugar.

In some embodiments, the methods of preparing an edible composition further comprise adding one or more additional components selected from the group consisting of preservatives, nutritives, flavorants or flavor modifiers, which may lack an inherent flavor. In some embodiments, the methods of preparing an edible composition further comprise adding one or more additional flavor modifiers.

In some embodiments, the edible composition is a consumer product.

Method of Preparing a Food Product:

According to another aspect, the invention provides a method of preparing an edible composition, wherein the edible composition is a food product. The method comprises: (a) providing a foodstuff; and (b) adding to the foodstuff at least one sophorolipid disclosed herein. In some embodiments, the sophorolipid is added in the form of an edible composition comprising the sophorolipid.

In some embodiments, the foodstuff in (a) is inherently bitter. In such embodiments, the food stuff may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt. In some embodiments, the inherent bitter tastant is KCl. In other embodiments, the inherent bitter tastant is potassium lactate.

In some embodiments, the method comprises: (a) providing a food product; and (b) adding to the food product at least one sophorolipid disclosed herein. In some embodiments, the sophorolipid is added in the form of an edible composition comprising the sophorolipid.

In some embodiments, the food product in (a) comprises a bitter tastant. In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the method of preparing a food product further comprises: (c) adding a bitter tastant. In some embodiments, the bitter tastant is a potassium salt, such as KCl or potassium lactate. In specific embodiments, the potassium salt is KCl. In some embodiments, the bitter tastant is added before the sophorolipid. In other embodiments, the bitter tastant is added after the sophorolipid. In some embodiments, the sophorolipid is added with the bitter tastant. In some embodiments, the sophorolipid is combined with the bitter tastant and then combined with the foodstuff or food product. In other embodiments, the compound of the sophorolipid is combined sequentially with the foodstuff or food product and then the bitter tastant. In yet other embodiments, the compound of the sophorolipid is combined with a mixture of the bitter tastant and the foodstuff or food product.

In some embodiments, the sophorolipid and the bitter tastant, if present, are mixed with the foodstuff. In other embodiments, the sophorolipid and the bitter tastant, if present, are sprayed onto or coat the foodstuff. In some embodiments, the sophorolipid is plated on a carbohydrate or salt, encapsulated on a salt or a carbohydrate (spray dried), or co-crystallized with a potassium salt to create a "topping" salt.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the food product further comprises a sodium salt. In some embodiments, the food product further comprises NaCl. In other embodiments, the food product further comprises sodium lactate. In further embodiments, the food product further comprises sugar.

In some embodiments, the methods of preparing a food product further comprise adding one or more additional components selected from the group consisting of preservatives, nutritives, flavorants or flavor modifiers, which may lack an inherent flavor.

Method of Preparing a Pharmaceutical Composition:

According to another aspect, the invention provides a method of preparing an edible composition, wherein the edible composition is a pharmaceutical composition. The method comprises: (a) providing a pharmaceutically active ingredient; and (b) adding to the pharmaceutically active ingredient at least one sophorolipid disclosed herein. In some embodiments, the sophorolipid is added in the form of an edible composition comprising the sophorolipid.

In some embodiments, the pharmaceutically active ingredient is inherently bitter. In such embodiments, the pharmaceutically active ingredient may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt.

In some embodiments, the method of preparing a pharmaceutical composition further comprises adding a bitter tastant. In some embodiments, the bitter tastant is a potassium salt. In some embodiments, the potassium salt is KCl or potassium lactate. In specific embodiments, the potassium salt is KCl. In some embodiments, the bitter tastant is added before the sophorolipid. In other embodiments, the bitter tastant is added after the sophorolipid. In some embodiments, the bitter tastant is added with the sophorolipid. In some embodiments, the sophorolipid is combined with the bitter tastant and then combined with the pharmaceutically active ingredient. In other embodiments, the sophorolipid is combined sequentially with the pharmaceutically active ingredient and then the bitter tastant. In yet other embodiments, the sophorolipid is combined with a mixture of the bitter tastant and the pharmaceutically active ingredient.

In some embodiments, the sophorolipid and the bitter tastant, if present, are mixed with the pharmaceutically active ingredient. In other embodiments, the sophorolipid and the bitter tastant, if present, are sprayed onto or coat the pharmaceutical composition. In some embodiments, the sophorolipid is encapsulated with the pharmaceutically active ingredient. In some embodiments, the sophorolipid is in a form such that the rate of release is regulated vis a vis the rate of release of the bitter tastant, which in some embodiments is the pharmaceutically active ingredient.

In some embodiments, the bitter tastant is a bitter tasting salt. In some embodiments, the bitter tastant, is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the pharmaceutical composition further comprises a sodium salt. In some embodiments, the pharmaceutical composition further comprises NaCl. In other embodiments, the pharmaceutical composition further comprises sodium lactate. In further embodiments, the pharmaceutical composition further comprises sugar.

In some embodiments, the pharmaceutical composition further comprises a pharmaceutically acceptable carrier. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the methods of preparing a pharmaceutical composition further comprise adding one or more additional components selected from the group consisting of preservatives, nutritives, flavorants or flavor modifiers, which may lack an inherent flavor.

Method of Reducing or Eliminating the Perception of Bitter Taste in a Subject:

According to another aspect, the invention provides a method of reducing or eliminating the perception of bitter taste in a subject. The method comprises the use of an edible composition comprising at least one sophorolipid disclosed herein.

The method can be used to reduce or eliminate bitter taste in any edible composition, including a foodstuff, food product, pharmaceutical composition or consumer product. The edible composition may be in any form. In some embodiments, the composition is in the form of, for example, a gum, lozenge, sauce, condiment, meat matrix, meat slurry, paste, suspension, spread, coating, a liquid, a gel, an emulsion, granules, or seasoning.

In some embodiments the edible composition is utilized by, for example, placement in the oral cavity or by ingestion. In some embodiments, the edible composition is placed in the oral cavity or ingested before a bitter food stuff, food product, pharmaceutical composition or consumer product. In some embodiments, the edible composition is placed in the oral cavity or ingested concurrently with a bitter food stuff, food product, pharmaceutical composition or consumer product, either as a separate edible composition or by incorporation in the bitter food stuff, food product, pharmaceutical composition or consumer product. In some embodiments, the edible composition is placed in the oral cavity or ingested after a bitter food stuff, food product, pharmaceutical composition or consumer product. For example, a compound of the invention can be combined with foodstuffs or food products to reduce the bitter taste of a food product. Alternatively, a sophorolipid can be used, for example, in a lozenge or gum for use after exposure to a bitter food stuff, food product, pharmaceutical composition or consumer product (e.g., to reduce or eliminate a bitter aftertaste).

Method of Reducing Bitter Taste of an Edible Composition:

According to another embodiment, the invention provides methods of reducing the bitter taste in an edible composition. In some embodiments, the edible composition is a food product. In some embodiments, the edible composition is a pharmaceutical composition. In some embodiments, the edible composition is a consumer product.

In one embodiment, the method comprises adding an effective amount of at least one sophorolipid disclosed herein to an edible composition such that bitter taste is reduced.

In alternate embodiments, the method comprises ingesting an effective amount of at least one sophorolipid disclosed herein before, along with, or after the edible composition such that bitter taste is reduced.

In some embodiments, the bitter tastant is a bitter tasting salt. In some embodiments, the bitter tastant is a potassium salt, a magnesium salt, or a calcium salt. In some embodiments, the bitter tastant, is a potassium salt. In some embodiments, the bitter tastant is KCl. In other embodiments, the bitter tastant is potassium lactate. In some embodiments, the bitter tastant is inherent in the edible composition, such as in an inherently bitter foodstuff.

In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 100%. These amounts are not meant to be limiting, and increments between the recited percentages are specifically envisioned as part of the invention. In some embodiments, the bitter taste is reduced by up to 25%. In other embodiments, the bitter taste is reduced by up to 50%. In other embodiments, the bitter taste is reduced by up to 75%. In other embodiments, the bitter taste is reduced by up to 100%. These amounts are not meant to be limiting, and increments between the recited percentages are specifically envisioned as part of the invention.

In some embodiments, the method of reducing the bitter taste attributed to a bitter tastant in an edible composition further comprises adding one or more additional components selected from the group consisting of preservatives, nutritives, flavorants or flavor modifiers (which lack an inherent flavor).

Method of Inhibiting a Bitter Taste Receptor:

According to another embodiment, the invention provides a method of inhibiting or reducing activation and/or signaling of a bitter taste receptor. In some embodiments, the method comprises contacting a bitter taste receptor with at least one sophorolipid disclosed herein. In some embodiments, the method comprises contacting a bitter taste receptor with at least one sophorolipid disclosed herein.

In some embodiments, the method comprises contacting a bitter taste receptor with an edible composition comprising at least one sophorolipid disclosed herein.

In some embodiments, the edible composition is a food product. In some embodiments, the edible composition is a pharmaceutical composition. In some embodiments, the edible composition is a consumer product.

In some embodiments, the bitter taste receptor is an ex vivo receptor present in, for example, an assay. In some embodiments, the bitter taste receptor is an in vitro receptor present in, for example, an assay. In other embodiments, the bitter taste receptor is an in vivo receptor present in a subject. In some embodiments, the bitter taste receptor is present in the oral cavity or gastrointestinal tract of a subject. In some embodiments, the bitter receptor is in the oral cavity of a human. In some embodiments, the bitter receptor is in the oral cavity of a non-human animal. In some embodiments, the bitter receptor is in the oral cavity of an animal model.

In some embodiments, inhibition of a bitter taste receptor will affect a physiological process or condition. Non-limiting examples of physiological processes and conditions affected by inhibition of bitter taste receptors include bitter taste, hypertension, nausea, emesis, effects on the gastrointestinal tract, appetite, nutrition, nutrient absorption, satiety, hunger, diabetes, obesity, blood glucose levels, blood glucose regulation, metabolism, diet, and eating disorders.

Method of Reducing the Amount of Sugar in an Edible Composition or Food Product:

According to another embodiment, the invention provides a method of reducing the amount of sugar in an edible composition. In some embodiments, the method comprises replacing an amount of sugar used in preparing an edible composition with an amount of at least one sophorolipid disclosed herein.

In some embodiments, the edible composition is a food product. In some embodiments, the edible composition is a pharmaceutical composition. In some embodiments, the edible composition is a consumer product.

Method of Reducing Sugar Intake of a Subject:

According to another embodiment, the invention provides a method of reducing sugar intake of a subject. In some embodiments, the method comprises the step of providing an edible composition of the present invention to the subject, wherein all or a portion of the sugar in the edible composition is replaced with at least one sophorolipid disclosed herein, and wherein the edible composition comprises at least one sophorolipid disclosed herein. In some embodiments, the edible composition is a food product. In some embodiments, the edible composition is a pharmaceutical composition. In some embodiments, the edible composition is a consumer product.

The following examples are intended only to further illustrate the invention and are not intended to limit the scope of the invention as defined by the claims.

Examples

Chemicals, Biochemicals, and Biologicals:

*Candida bombicola* ATCC 22214 was purchased from the American Type Culture Collection (Manassas, Va.) and stored at −80° C. in Luria-Bertani (LB) broth (1% tryptone, 0.5% NaCl, 0.5% yeast extract) supplemented with 15% (v/v) glycerol as a cryopreservative. Glucose, palmitic acid, oleic acid, stearic acid, and urea were all purchased from Sigma Chemical Company (St. Louis, Mo.). Bacto-tryptone and Bacto Yeast Extract (components of LB broth and *Candida* Growth Media (CGM)) were purchased from Becton Dickinson (Sparks, Md.). Ethyl acetate and hexane (both HPLC grade) were purchased from Burdick & Jackson (Muskegon, Mich.).

Production and Characterization of $C_{18}/C_{16}$-Sophorolipids.

Fermentation: Sophorolipids were produced at the 10-L bench-top scale from *C. bombicola* ATCC 22214 grown on glucose and either palmitic acid, oleic acid, or stearic acid. The basal CGM (10% glucose, 1% yeast extract, 0.1% urea) was prepared, sterilized by autoclave, and the temperature was equilibrated to 26° C. Fatty acid was added to the CGM as the lipid co-substrate, either as insoluble solids (palmitic acid, stearic acid) or as non-miscible liquids (oleic acid) at a final concentration of 2% by weight. One 50-mL frozen inoculum culture was thawed and used to inoculate each fermentation. The fermentations were conducted at a temperature of 26° C., an agitation rate set at 700 rpm, an air-flow rate of 2 L of air/min, and no pH control. After 2 days, an additional 7.5% (w/v) of dry glucose and 2% (w/v) fatty acid were added to the fermentations and the fermentations allowed to proceed to 5 days when an additional 0.5% (w/v) of fatty acid was added. The fermentations then continued for an additional 2 days (total duration of the fermentation was 7 days).

Product Recovery:

Sophorolipid isolation and recovery was accomplished by lyophilizing the entire culture to dryness for ~2 days. The dried residue was divided and placed into three 6-L Erlenmeyer flasks. Each fraction was extracted with excess ethyl acetate at room temperature for two days. The extract was filtered through Whatman No. 2 filter paper to remove any insoluble material (e.g., residual yeast cells). The remaining solids were washed two additional times with ethyl acetate to maximize recovery. The ethyl acetate fractions were combined, concentrated by evaporation, and precipitated into 1 L aliquots of hexane to obtain the pure SL. The pure SL was recovered from the hexane by filtration (described above) and vacuum-dried in a desiccator to obtain a fine white to off-white colored powder. Yield was determined gravimetrically.

Product Analysis:

The SL content was determined as described previously (Nuñez et al. 2001). The SL mixtures were separated by HPLC with a Waters 2690 Separation Module (Waters Company) using a 5 cm×2.1 mm and a 15 cm×2.1 mm Symmetry C18 3.5 am column coupled in series. The linear gradient elution used was as follows: water:acetonitrile (0.5% formic acid):acetonitrile (50:10:40), hold for 5 minutes; to a final composition of water: acetonitrile (0.5% formic acid:acetonitrile (40:10:50) over 25 minutes; with a total running time of 50 minutes. The flow rate was 0.25 mL/min. The effluent was connected to a Micromass ZMD mass spectrometer with an APCI probe (Waters) set to the positive mode to scan from m/z 200 to m/z 1000 at 2 seconds per scan. Corona pin voltage was tuned to 3.8 kV, sample cone 20 V, and extraction cone 2 V for detection of fragments and molecular ions ([M]+).

In Vitro Cell-Based Assay of Sweet Property.

Establishment and maintenance of cultures of human fungiform taste papillae cells (HBO cells): We previously established the current proprietary protocol (Ozdener, H., et al., Chem. Senses, 31(3): 279-90 (2006); Ozdener, M. H., et al., Chem. Senses, 36(7): 601-12 (2011); Ozdener, H., et al., Isolation and culture of human fungiform taste papillae cells, J. Vis. Exp., 2012 May 17; (63):e3730) which allowed us to culture human fungiform taste papillae cells retaining their physiological and molecular characteristics for more than a year. We previously demonstrated that HBO cells closely resembled composition of taste buds in vivo: they are heterogeneous and include taste receptor cells tuned to respond to basic taste qualities (bitter, sweet, salty, sour, umami).

The human fungiform taste papillae cells were cultured according to protocols that we have published (Ozdener et al. 2006, Ozdener et al. 2011). Human fungiform taste papillae were removed and immediately placed into an isolation solution followed by enzymatic digestion. Digested fungiform papillae were then gently minced with a surgical razor and seeded on collagen type-1 coated coverslips and incubated at 36° C. in a humidified environment containing 5% $CO_2$. The fungiform taste papillae cells were cultured in Iscove's Modified Dulbecco's medium containing 10% fetal bovine serum, 1:5 ratio of MCDB (Molecular, Cellular, and Developmental Biology) 153 medium, and a triple cocktail of antibiotics (100 U/mL/100 jag/mL, penicillin/streptomycin, and 0.5 µg/mL fungizone). Culture medium was replaced every 5-7 days by one-third of fresh culture medium. Human fungiform taste papillae cells have been maintained in culture for a period of more than 1 year without loss of viability and with retention of the molecular and biochemical properties of acutely isolated taste cells (Ozdener et al., 2011).

Calcium Imaging:

Cultured taste cells grown for 3-4 days glass coverslips which were loaded for 30-60 min with the calcium sensitive dye fura-2 by incubating the cells in Ringer solution (145 mM NaCl, 5 mM KCl, 1 mM $MgCl_2$, 1 mM $CaCl_2$, 1 mM Na-pyruvate, 20 mM Hepes-Na and Cellobiose 15 mM, pH 7.2 with osmolarity adjusted to 300-310 by 5M NaCl) supplemented with 1 mM Fura-2 AM (Molecular Probes Inc., Eugene, Oreg.) and 10 mg/ml Pluronic® F127 (Molecular Probes Inc.). Coverslips were then placed in a recording chamber and continuously bathed with Ringer solution superfusion. Stimuli were dissolved in Ringer and then pH and osmolarity readjusted if needed. Cells were exposed to sweet (Sucrose 2%) Sucralose (1 mM), bitter mixture (PTC (phenylthiocarbamide)) 2 mM+Salicin 5 mM+Denatonium 2 mM), guaifenesin (GF, 3 mM) and acetaminophen (APAP, 3 mM), and various sophorolipids stimuli: sophorose, sophorolipid palmitic acid, sophorolipid stearic acid, sophorolipid oleic acid. The chemical stimuli were applied to the coverslip by switching the superfusion to the stimulus solution, which allowed for a complete change of bath solutions in the chamber within 10 s. Calcium imaging recordings were performed using standard imaging techniques (Rawson, N. E., et al., J. Neurophysiology, 77(3): 1606-1613 (1997)). Illumination was via a Metamorph software (Molecular Devices) monochromator coupled to the microscope. Cells were illuminated with light emitted by a 75-W Xenon lamp alternately filtered with narrow band-pass filters at 340 nm, then 380 nm. Emitted light from the fura-2 in the cells under 200× microscopic magnification was filtered at 510 nm and passed through an image intensifier coupled with a cooled CCD camera (Olympix, Perkin Elmer Life Sciences, Bethesda Md.). Exposure times were minimized and light shuttered between acquisitions to minimize photobleaching. Cells remained viable in the recording setup for over 2 h without visible effects of dye bleaching. Stimuli were diluted in Ringer buffer and applied via a gravity-flow superfusion apparatus for 10-60 s, depending on the stimulus.

Determination of Sweet Potency of Sophorolipids and Sophorose:

We utilized human taste cell culture to determine dose related response frequency induced by sucralose and sophorolipids and sophorose. To examine the sweet potency of sophorolipids, we examined the most commonly used artificial sweetener, sucralose (Splenda®), as standard sweet molecule. The results obtained from sucralose (5 mM) were compared to the response frequency of sophorolipids induced in culture taste cells. Adjusted results were optimized based on concentration vs. response frequency.

Mouse Model for Sweet Property and Bitter-Masking Assay.

Recordings of chorda tympani (CT) whole-nerve responses: All protocols involving animals were approved by the Institutional Animal Care and Use Committees at the Monell Center prior to the experiments. The study was performed with mice from two strains: C57BL/6J inbred strain (B6; Jackson Laboratory, Bar Harbor, Me.) bearing the wild-type Tas1r3 allele was used as the control, and the C57BL/6J-Tas1r3$^{tm1Rfm}$ "gene-knockout" strain (T1R3-KO) lacking the entire T1R3 coding region and devoid of T1R3 protein (Damak, S., et al., Science, 301: 850-853 (2003)). Afferent signals from taste cells are relayed to the brain via three major gustatory nerves: the chorda tympani, glossopharyngeal, and greater superficial petrosal. To directly examine effects of Tas1r3 genotype on peripheral taste input, we examined responses of the chorda tympani nerve to lingual application of taste stimuli. The chorda tympani nerve was chosen for this study for the following reasons: First, in mice it has a high proportion of sucrose-best fibers (Ninomiya, Y., and M. Funakoshi, Comp. Biochem. Physiol., 92: 371-376, 1989 (1989)) and responds robustly to gustatory stimulation with sweeteners (Damak et al. 2003; Danilova, V., and G. Hellekant, BMC Neurosci., 4: 5 (2003); Inoue, M., et al., Chem. Senses, 26: 915-923 (2001); Ninomiya, Y., et al., Neurosci. Lett., 163: 197-200 (1993); Shingai, T., and L. M. Beidler, Brain Res., 335: 245-249 (1985)). Second, the Tas1r3 gene is expressed in taste cells throughout the oral cavity, including the anterior part of the tongue (Kitagawa, M., et al., Biochem. Biophys. Res. Commun., 283: 236-242 (2001); Max, M., et al., Nat. Genet., 28: 58-63 (2001); Montmayeur, J, P., et al., Nat. Neurosci., 4: 492-498 (2001); Nelson, G., et al., Cell, 106: 381-390 (2001); Reed, D. R., et al., J. Neurosci., 24: 938-946 (2004); Sainz, E., et al., J. Neurochem., 77: 896-903 (2001)), which is innervated by the chorda tympani nerve. We therefore expected that deletion of the Tas1r3 gene would affect chorda tympani responses to sweeteners.

Procedure:

Mice were anesthetized with sodium pentobarbital (50-60 mg/kg of body weight, intraperitoneally, with further doses as necessary). A cannula was inserted in the trachea, and the animal was placed supine in a non-traumatic headholder. The right chorda tympani nerve was exposed at its exit from the lingual nerve by removal of the internal pterygoid muscle. The chorda tympani nerve was then dissected free from surrounding tissues and cut at the point of its entry to the bulla. The entire chorda tympani nerve was placed on a platinum wire electrode, and a few drops of mineral oil were placed in the wound site to prevent desiccation of the nerve. An indifferent electrode was positioned in nearby muscle tissue. Neural responses resulting from chemical stimulations of the tongue were fed into an amplifier (Grass Instruments, West Warwick, R.I.) and monitored on an oscilloscope and an audio monitor. Whole-nerve responses were integrated with a time constant of 1.0 s and recorded using a computer for later analysis using a PowerLab system (PowerLab/sp4; AD Instruments, Colorado Springs, Colo.). For chemical stimulation of the fungiform taste papillae, the anterior one-half of the animal's tongue was enclosed in a flow chamber. Solutions at room temperature (22° C.) were delivered into the flow chamber by gravity flow at a rate of 0.5 ml/sec for 30 sec. Between taste stimuli, the tongue was rinsed with deionized water for at least 1 min. Ammonium chloride ($NH_4Cl$) at 100 mM was presented frequently throughout recording to serve as a reference stimulus.

To analyze nerve responses to each stimulus, the magnitudes of integrated responses at 5, 10, 15, 20, and 25 s after stimulus onset were measured and averaged. The magnitude of the integrated response to each taste stimulus was expressed as a proportion of the response to 100 mM $NH_4Cl$ (applied both before and after the taste stimulus recording and averaged).

Results and Discussion.

Figure 2:
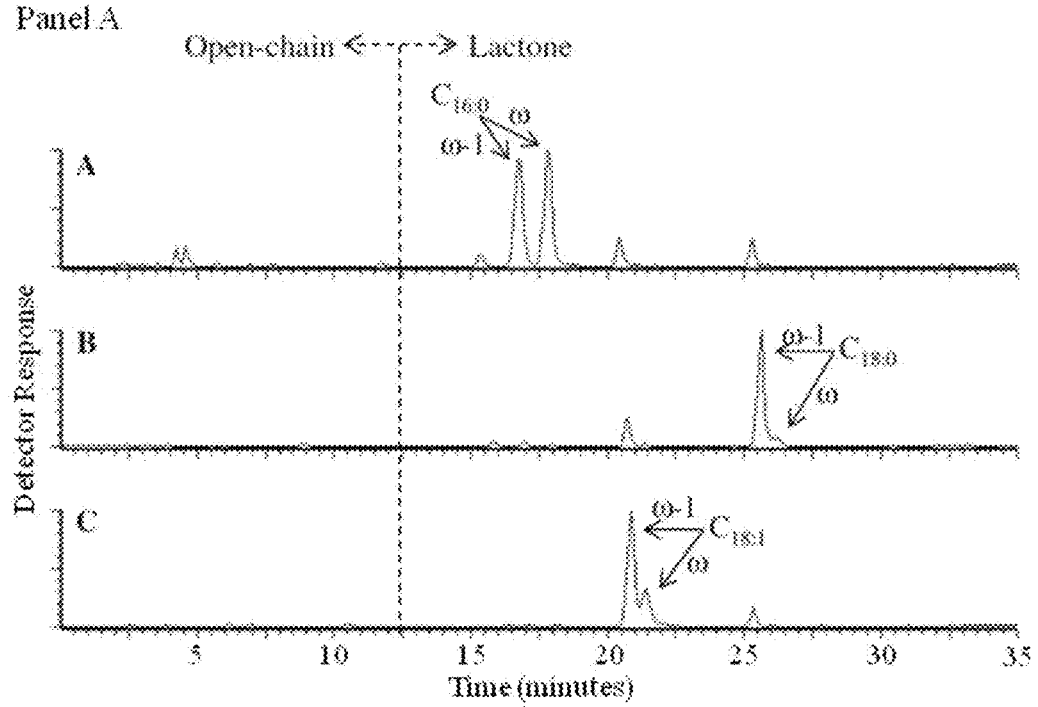
FIG. 2 shows LC-MS (liquid chromatography-mass spectrometry) analysis of SLs ((A) C16-SL; (B) C18-SL; (C) C18:1-SL)) as described below. Panel A (top), total ion chromatograms; Panel B (bottom), atmospheric pressure chemical ionization-mass spectra.
Figure 2:
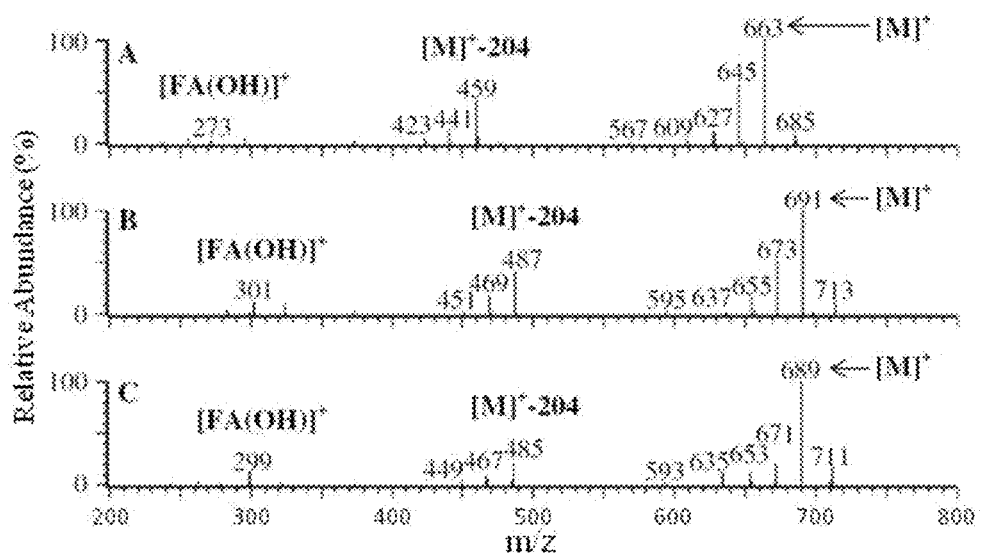
Figure 3:
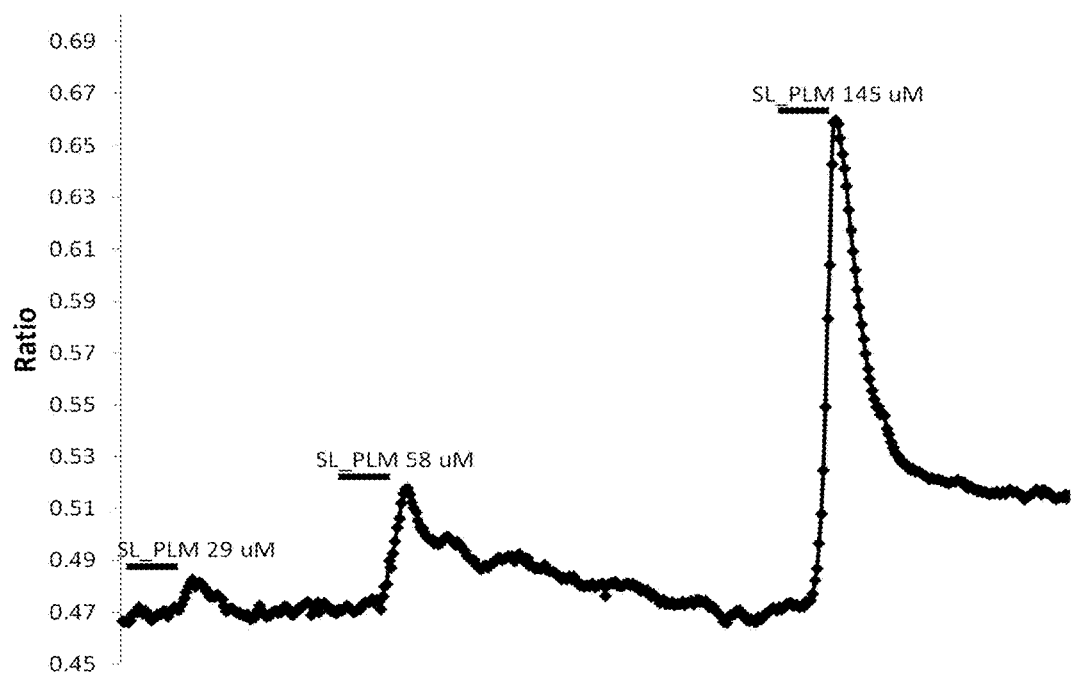
FIG. 3 shows stimulation of cultured human taste papillae (HBO) cells by C16-SL as described below. Three different concentrations (29 µM, 58 µM and 145 µM) of C16-SL (also known as SL_PLM) dissolved in dimethyl sulfoxide (DMSO) were tested in HBO cells. It was determined that 145 µM of C16-SL was the optimal concentration for evoking $Ca^{+2}$ responses. The graph represents average responses of 89 cells.

Production and Characterization of Sophorolipids: Structurally varied sophorolipids were produced by C. bombicola when different fatty acid was added to the culture broth during fermentation (Ashby et al. 2008). The addition of palmitic acid (a fatty acid with a 16-carbon chain backbone) resulted in the synthesis of sophorolipids in which the hydrophobic moiety consists of a 16-carbon fatty acid unit (C16-SL) as determined by LC-MS (FIG. 2). Similarly, the addition of stearic acid (18-carbon chain) or oleic acid (18-carbon chain but containing one unsaturated or double bond) yielded sophorolipids with an 18-carbon chain containing, respectively, 0 (C18-SL) and 1 (C18:1) double bond as the hydrophobic moiety was confirmed by LC-MS analysis (FIG. 2). The volumetric yields of the isolated materials were 42 g/l, 77 g/l, and 98 g/l for C16-SL, C18-SL, and C18:1-SL, respectively (Ashby et al. 2008). It should be noted that from here on, C16-SL refers to sophorolipids containing 16-carbon chain fatty acid unit and was produced using palmitic acid; C18-SL contains 18-carbon chain fatty acid and was produced using stearic acid; and C18:1-SL contains 18-carbon chain fatty acid having one unsaturated bond and was produced using oleic acid.

Figure 4:
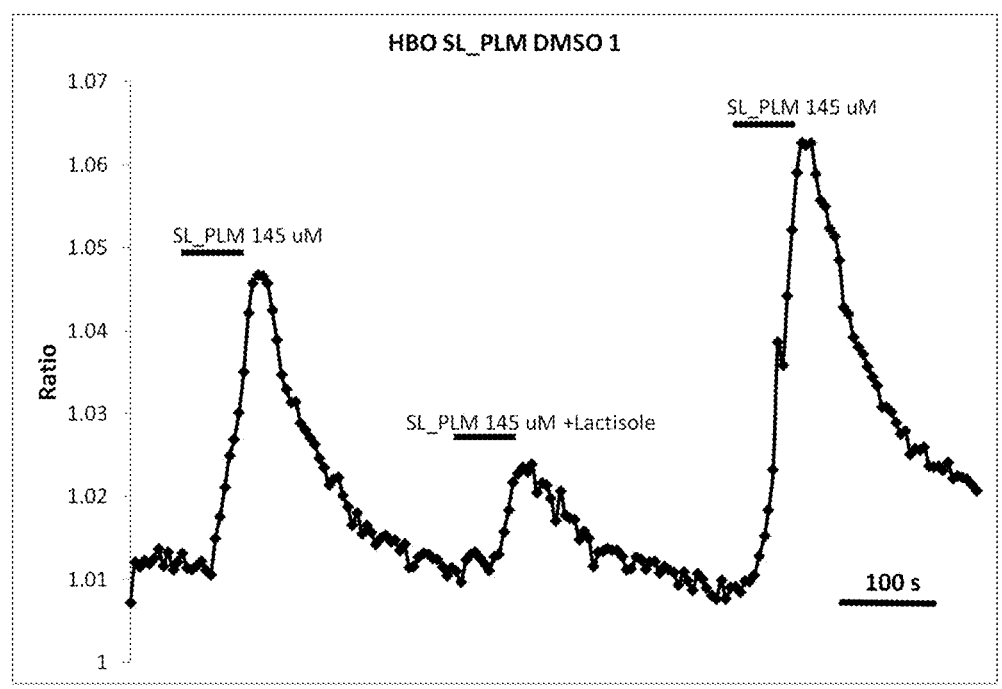
FIG. 4 shows response of lactisole-sensitive cultured HBO cells to C16-SL as described below. C16-SL-induced responses averaged across the C16-SL (a.k.a. SL_PLM)-responsive cells (n=29) were suppressed by lactisole which suggested that C16-SL-induced responses were mediated by a sweet receptor (T1R2+T1R3).
Figure 5:
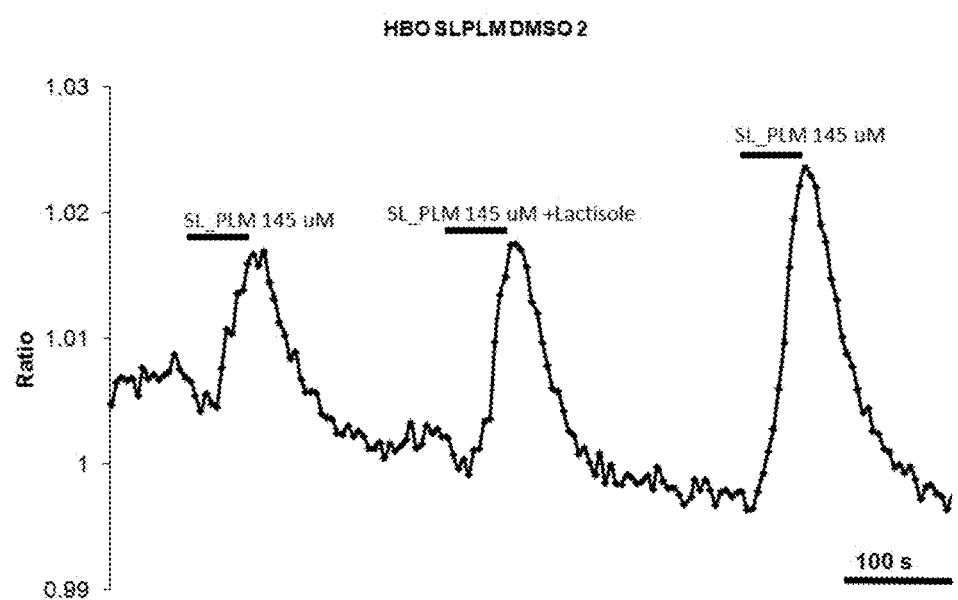
FIG. 5 shows response of lactisole-insensitive cultured HBO cells to C16-SL as described below. Average responses (n=54) in cells in which C16-SL (a.k.a. SL_PLM)-induced responses were not blocked by lactisole. This suggested that C16-SL activated in these cells either the T1R3-independent sweet transduction pathway or the non-sweet taste (e.g., bitter).
Figure 8A:
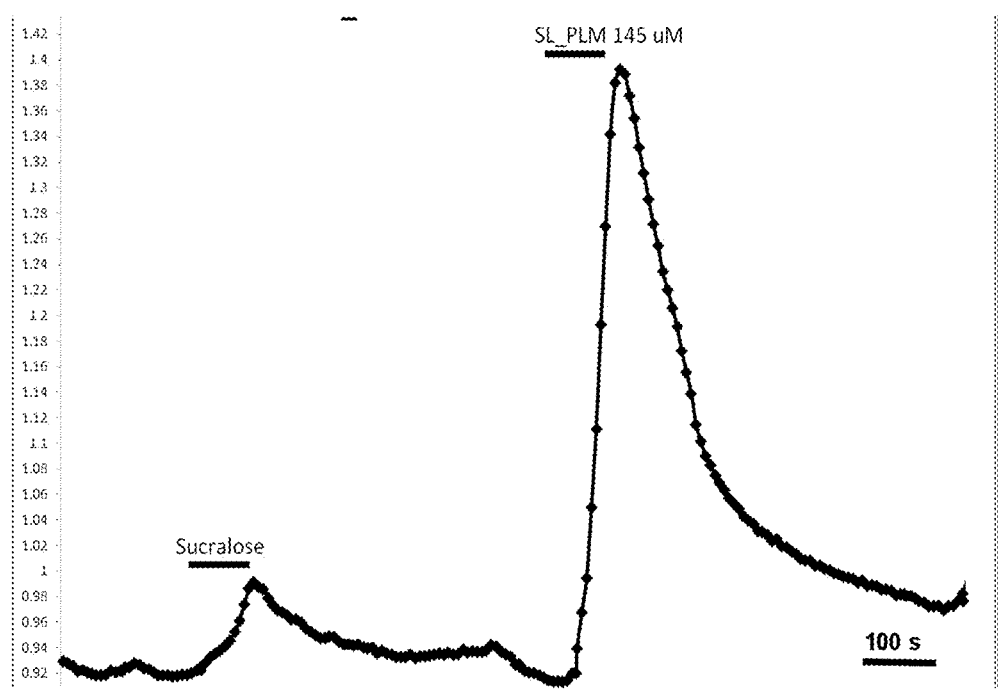
FIG. 8A shows sophorolipid responsive cells may also be responsive to sweet in cultured taste papillae cells and FIG. 8B shows sophorolipid responsive cells may also be responsive to bitter stimuli in cultured taste papillae cells as described below.

Assessment of Sweet Properties of Sophorolipids in In Vitro and In Vivo Assays:

We examined taste properties of sophorolipids (i.e., C16-SL, C18-SL, and C18:1-SL) and sophorose (i.e., only the disaccharide sugar) using cultured HBO cells. To determine whether sophorolipids have a sweet taste and/or other taste characteristics (for instance a bitter taste), we applied molecules with well characterized taste properties (natural and artificial sweetener and bitter) along with sophorolipids to determine the relation between the cells responsive to sophorolipids and cells responsive to other taste modalities. We demonstrated that sophorose and sophorolipid responsive cells were also found responsive to sweet stimuli (FIG. 8A). We additionally showed that the majority of the sophorose and sophorolipids responsive cells were lactisole sensitive which means that sophorolipids utilized sweet taste receptor called T1R3, and therefore its specific blocker (i.e., lactisole) suppresses the effect of sophorolipids (FIG. 4). Therefore, it was concluded that the activation of sweet-responsive cells by sophorose and sophorolipids was mediated by the T1R3 taste receptor.

Figure 6A:
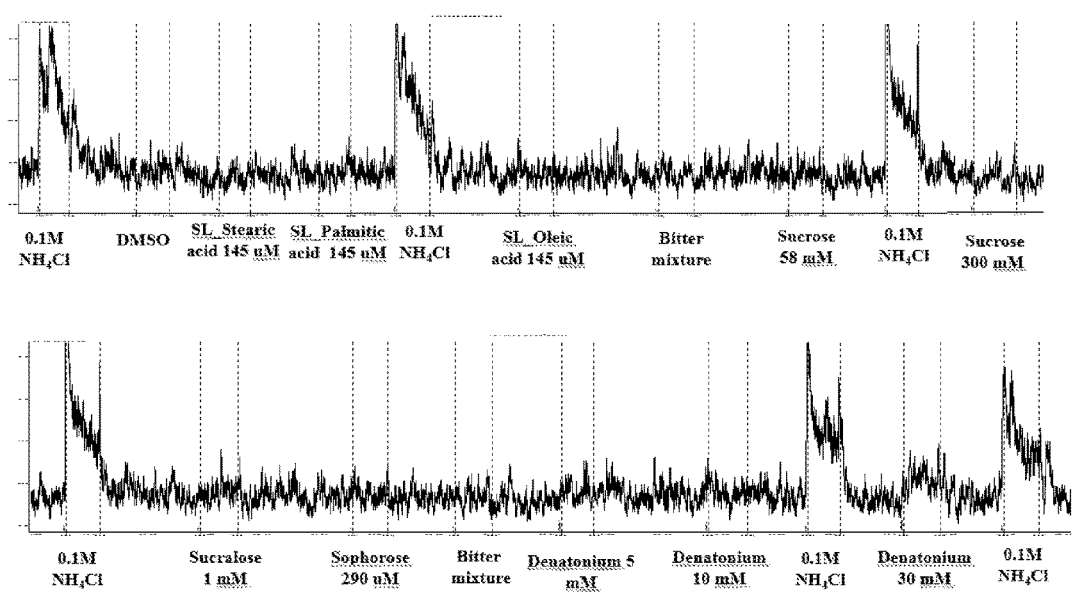
FIG. 6A and FIG. 6B shows chorda tympani responses to SLs as described below.
Figure 6B:
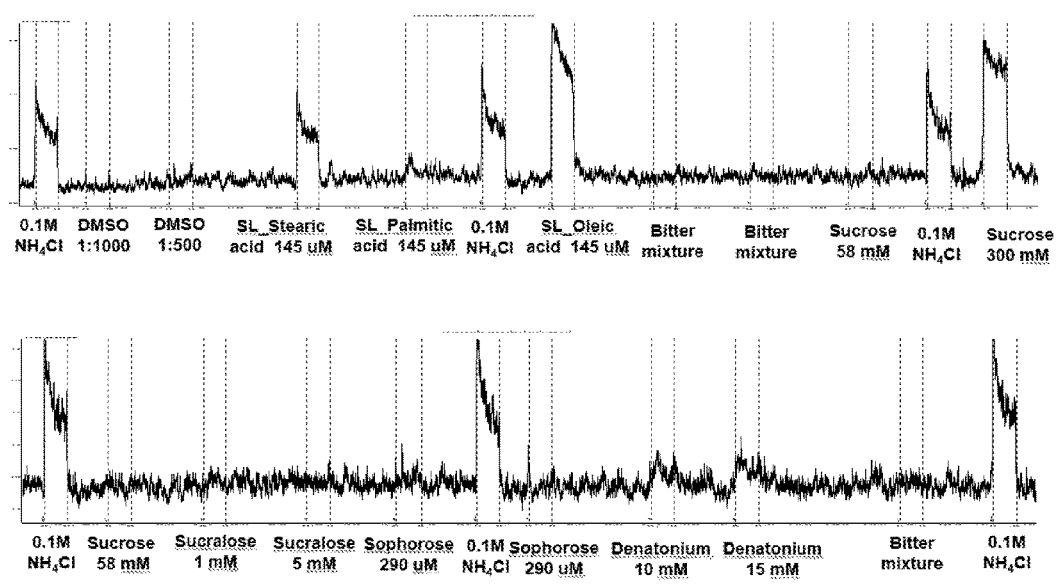
Figure 7:
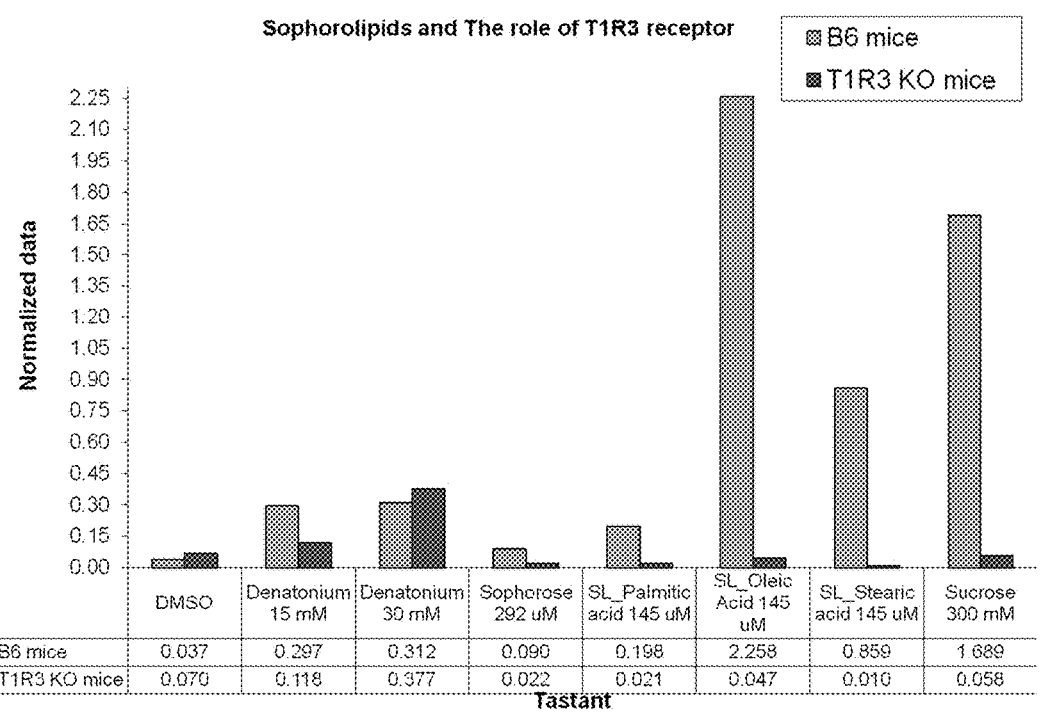
FIG. 7 shows chorda tympani responses to SLs and control taste stimuli in T1R3-KO and wild-type B6 mice as described below. Chorda tympani responses to sucrose, sophorose, and three SLs were present in wild type B6 mice but were nearly absent in T1R3-KO mice. This suggested that these compounds utilized T1R3 receptor. Magnitude of responses to different SLs varied, suggesting that they differ in sweetness intensity.

To elucidate the function and the contribution of T1R3 to sophorose and sophorolipid taste detection in vivo, we used knock-out (T1R3(−/−)) mice. Gustatory nerve (chorda tympani nerve) recordings demonstrated that T1R3(−/−) mice exhibited a serious deficit in sophorose- and sophorolipid-elicited synergy in chorda tympani nerves (FIG. 6A). In comparison, the wild-type mouse responded positively to sophorolipids (FIG. 6B). These data are summarized in FIG. 7. The animal study confirmed that sophorose and the sophorolipids act by interacting with the T1R3 receptor of taste cells.

We also examined the potency of sophorose and the sophorolipids using cultured human taste cells by comparing the cell's responses to sophorose and sophorolipids and responses of the same cells to a well-known sweet stimulus, sucralose (FIG. 8A). We found that sophorolipids concentration which evoked responses in this experiment was surprisingly very low (micromolar level), indicating potency of the sophorolipids and sophorose compared to the other stimuli. Sucralose is about 600 times sweeter than sucrose. Our result demonstrated that the sophorolipids were surprisingly about at least 2000 and 250 times sweetener compared to sucralose and sophorose, respectively (Table 1).

Figure 8B:
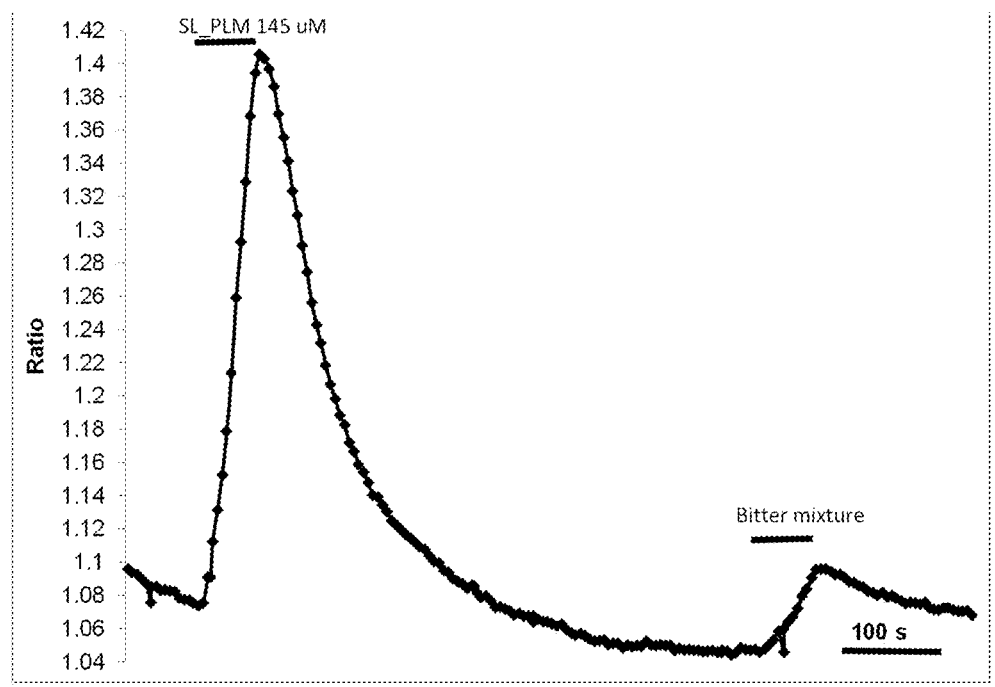
Figure 9:
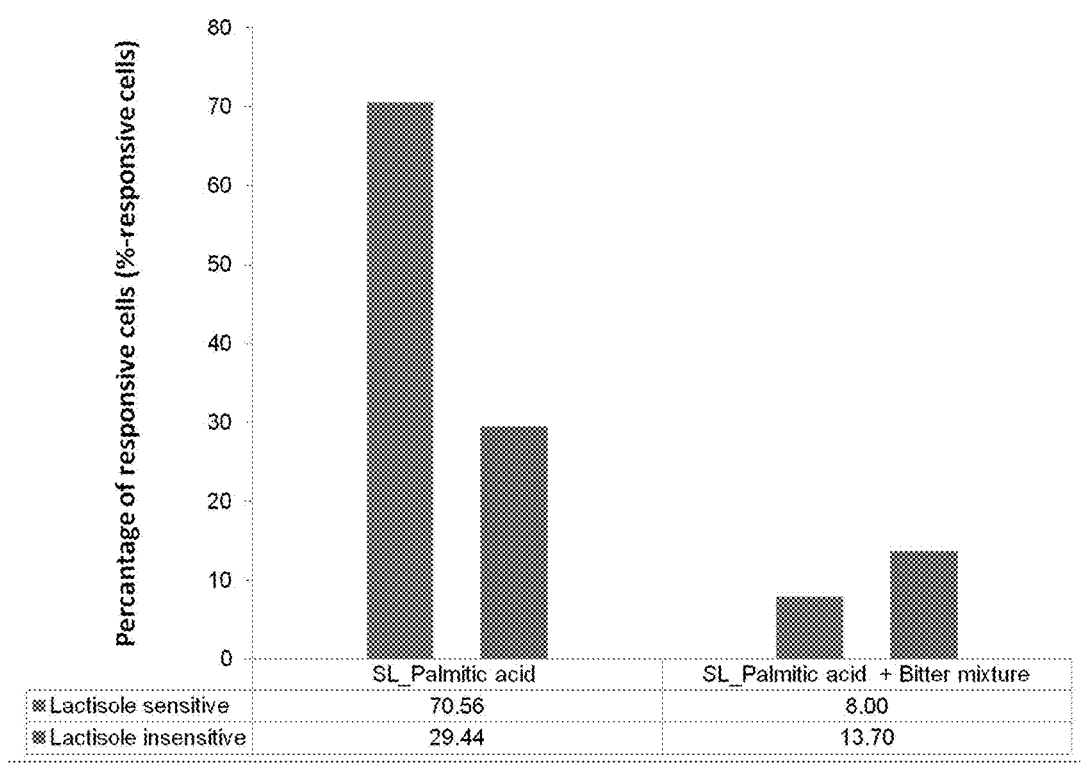
FIG. 9 shows majority of lactisole insensitive sophorolipid responsive cells were also responsive to bitter stimuli as described below.

Bitter-Masking Properties of Sophorolipids:

A small number of sophorose and sophorolipid responsive cells, however, were also found responsive to bitter stimuli (FIG. 8B). We observed that lactisole insensitive cells may overlap with bitter responsive cells and we noticed that the majority of lactisole insensitive cells were also found responsive to bitter (FIG. 9).

Figure 10A:
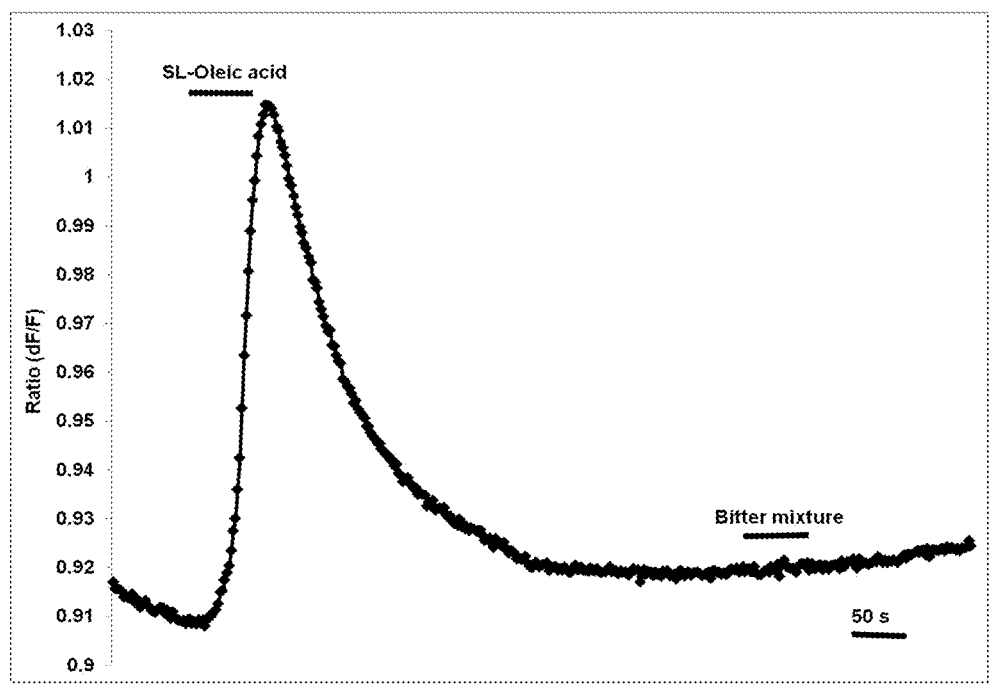
FIG. 10A shows application of the sophorolipids before the application of bitter mixture demonstrated complete elimination of bitter responses, though
Figure 10B:
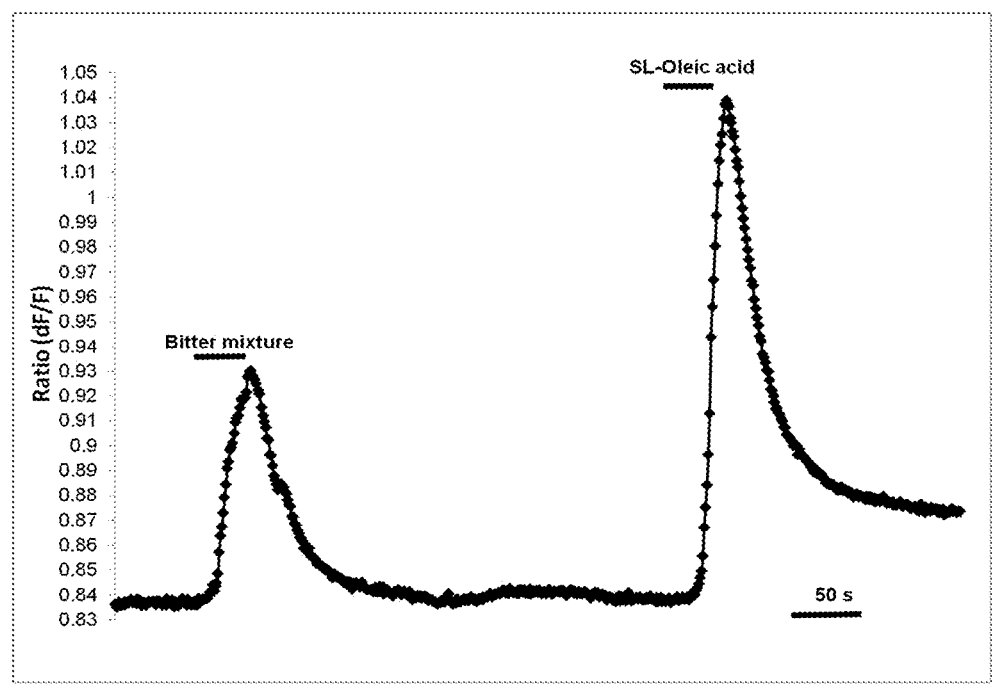
FIG. 10B shows application of bitter stimuli before application of sophorolipid did not eliminate the response to sophorolipids as described below.
Figure 11:
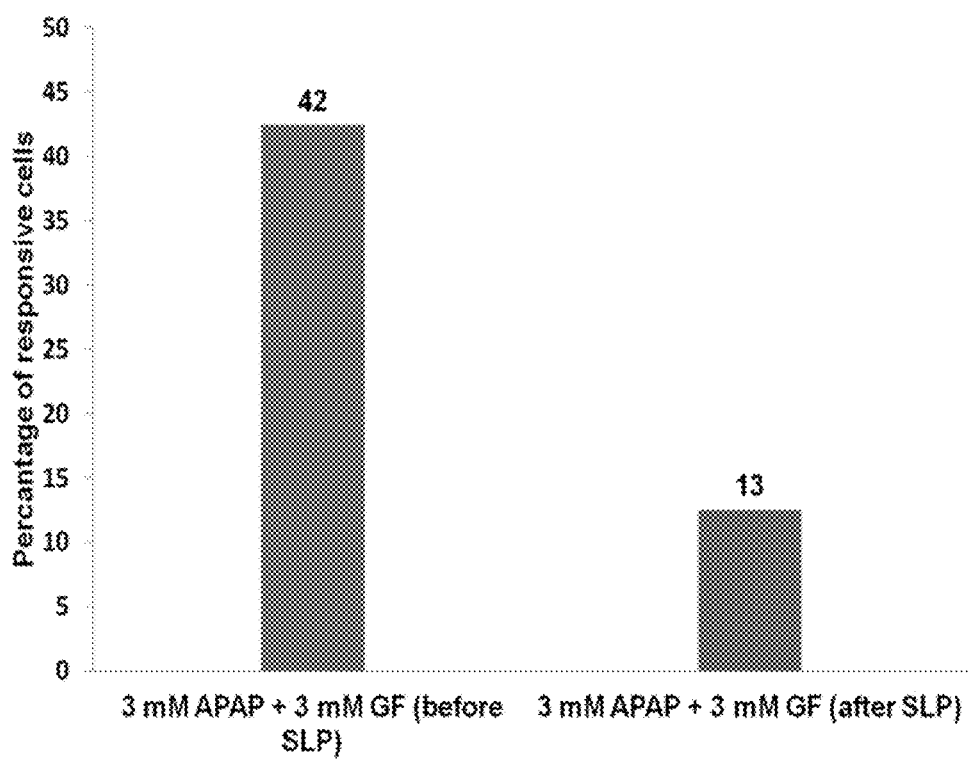
FIG. 11 shows application of the sophorolipid before the application of bitter tasting drug (acetaminophen (APAP) and guaifenesin (GF)) mixture demonstrated significant inhibition of bitter responses as described below. Intracellular calcium responses of cultured human taste cells to a mixture of two bitter-tasting medicines, acetaminophen (APAP) and guaifenesin (GF), before and after application of the sophorolipid_oleic acid. Sophorolipid_oleic acid application significantly (p<0.0000 test for significance of two proportions) reduced percentage of cells responding to APAP+GF.
Figure 12:
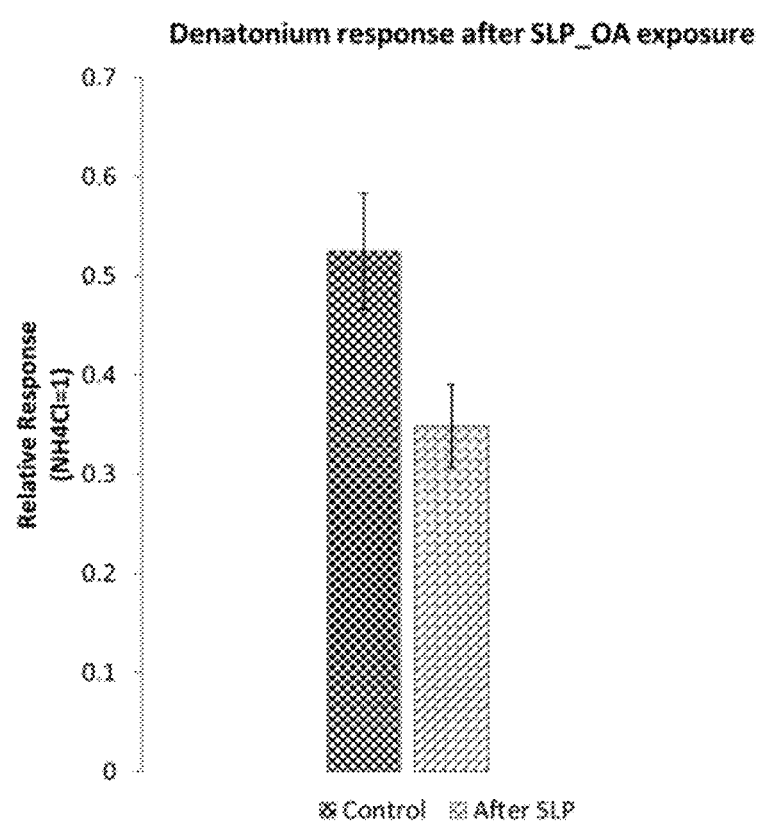
FIG. 12 shows mice chorda tympani nerve recordings demonstrated that application of the sophorolipid before the application of bitter mixture demonstrated significant reduction of bitter responses as described below. Integrated activity in the gustatory nerve (chorda tympani nerve) of wild-type mice in response to oral stimulation with 30 mM denatonium before and after application of the sophorolipid. Responses to 30 mM denatonium (after SLP (sophorolipids)) after sophorolipid application were significantly lower that responses to 30 mM denatonium (Control) before sophorolipid application.

Bitter taste of medicines and other molecules which humans consume is a major challenge for health and for the pharmaceutical industry. Using calcium imaging technique, we demonstrated that application of the sophorolipids before the application of bitter mixture surprisingly eliminated responses to bitter mixture in cultured human taste cells, indicating bitter blocking properties of the sophorolipids (FIG. 10A), while cells responded to bitter mixture if it was applied before sophorolipids (FIG. 10 B). Similar effect of the sophorolipids was surprisingly observed with another bitter stimulus, a mixture of two bitter-tasting oral medicines, acetaminophen (APAP) and guaifenesin (GF). The initial application of the APAP+GF mixture before sophorolipid application elicited intracellular calcium responses in cultured human taste cells; surprisingly responses to APAP+GF mixture applied after sophorololipid application were significantly reduced (FIG. 11), again indicating bitter blocking properties of the sophorolipids. To examine an effect of sophorolipids on bitter taste responses in vivo, we measured responses in the gustatory nerve (chorda tympani nerve) of anesthetized wild-type mice (FIG. 12). Nerve responses to oral application of denatonium (30 mM) were significantly lower after the sophorolipid application than they were before sophorolipid application. The significant reduction of bitter responses surprisingly indicated bitter blocking properties of the sophorolipids in vivo.

All of the references cited herein, including U.S. Patents, are incorporated by reference in their entirety. Also incorporated by reference in their entirety are the following U.S. Pat. Nos. 8,865,779; 8,992,892; 9,040,089; 8,986,735; 8,445,692; 8,895,051; 4,305,961. Also incorporated by reference in its entirety U.S. Patent Application Publication 2015/0237900. Also incorporated by reference in their entirety are the following: Baiano, A., Molecules, 19(9): 14821-42 (2014); Bhise, K., et al., AAPS PharmSciTech., 9(2): 557-562 (2008); Cardoso, J. M. P., and H. M. A. Bolini, J. Sensory Studies, 23: 804-816 (2008); Chan, P., et al., Br. J. Clin. Pharmacol., 50: 215-20 (2000); Hu, F. B., and S. M. Vasanti, Physiol. Behav., 100(1): 47-54 (2010); Grembecka, M., Rocz. Panstw. Zakl. Hig., 66(3): 195-202 (2015); Jaber, L., et al., PLoS ONE, 9(11): e112152 (2014); Karaman, R., Drug Des., 2: e116 (2013); Kinnamon, S. C., Acta Physiol. (Oxf)., 204(2): 158-68 (2012); Kobayashi, Y., et al., Lett. Appl. Microbiol., 60(5): 475-80 (2015); Ladrière, L., et al., Eur. J. Pharmacol., 344(1): 87-93 (1998); Laffitte, A., et al., Functional roles of the sweet taste receptor in oral and extraoral tissues, Curr. Opin. Clin. Nutr. Metab. Care, 2014; Lemus-Mondaca, R., et al., Food Chem., 132: 1121-1132 (2012); Lindley, M. G., Natural High-Potency Sweeteners, in Sweeteners and Sugar Alternatives IN Food Technology, Second Edition (eds K. O'Donnell and M. W. Kearsley), Wiley-Blackwell, Oxford, U K, 2012, doi: 10.1002/9781118373941.ch9; Ozdener, M. H., and N. E. Rawson, Methods Mol. Biol., 945: 95-107 (2013); Philippe, R. N., et al., Curr. Opin. Biotechnol., 26: 155-61 (2014); Riva, S., et al., Ann. N. Y. Acad. Sci., 864: 70-80 (1998); Riva, S., J. Molec. Cat. B: Enzymatic, Volumes 19-20, 2 Dec. 2002, Pages 43-54; Sclafani, A., et al., Chem. Senses, 35: 433-43 (2010); Shingai, T., and L. M. Beidler, Brain Res., 335: 245-249 (1985); Tandel, K. R., J. Pharmacol. Pharmacother., 2(4): 236-43 (2011).

Thus, in view of the above, there is described (in part) the following:

A composition comprising at least one sophorolipid selected from the group consisting of C16-SL, C18-SL, and C18:1-SL; and optionally a carrier; wherein the composition is edible. The above composition, further comprising a bitter tastant. The above composition, wherein said carrier is selected from the group consisting of a food product, a consumer product, and a pharmaceutical composition.

A composition comprising a bitter tastant and at least one sophorolipid (e.g., selected from the group consisting of C16-SL, C18-SL, C18:1-SL) and optionally a carrier; wherein the composition is edible and wherein the bitter taste of said bitter tastant is reduced compared to composition without sophorolipid. The above composition, wherein said bitter tastant is selected from the group consisting of a food product, a consumer product, and a pharmaceutical composition. The above composition, wherein said carrier is selected from the group consisting of a food product, a consumer product, and a pharmaceutical composition.

A pharmaceutical composition comprising the above composition of claim 1, and optionally a bitter tastant.

A pharmaceutical composition comprising a bitter tasting pharmaceutical active ingredient and at least one sophorolipid (e.g., selected from the group consisting of C16-SL, C18-SL, and C18:1-SL) and optionally a carrier.

A pharmaceutical composition comprising a pharmaceutical active ingredient, a bitter tastant, at least one sophorolipid (e.g., selected from the group consisting of C16-SL, C18-SL, and C18:1-SL) and optionally a carrier.

A consumer product comprising the above composition, and optionally a bitter tastant.

A consumer product comprising a bitter tasting ingredient and at least one sophorolipid (e.g., selected from the group consisting of C16-SL, C18-SL, and C18:1-SL) and optionally a carrier.

A food product comprising the above composition, and optionally a bitter tastant.

A food product comprising a bitter tasting ingredient and at least one sophorolipid (e.g., selected from the group consisting of C16-SL, C18-SL, and C18:1-SL) and optionally a carrier.

A method of inhibiting or reducing the bitter taste due to a bitter tastant, wherein the method comprises placing the above composition in the oral cavity of a subject.

A method of reducing bitter taste attributed to a bitter tastant in an edible composition, said method comprising adding to said edible composition an effective amount of at least one sophorolipid (e.g., selected from the group consisting of C16-SL, C18-SL, and C18:1-SL) and optionally a carrier; such that any bitter taste induced by the bitter tastant is reduced.

A method of inhibiting, reducing, or eliminating a bitter taste in a subject, said method comprising placing in the oral cavity of the subject an effective amount of at least one sophorolipid (e.g., selected from the group consisting of C16-SL, C18-SL, and C18:1-SL) and optionally a carrier.

A method of inhibiting a bitter taste receptor, said method comprising contacting the bitter taste receptor with composition an effective amount of at least one sophorolipid (e.g., selected from the group consisting of C16-SL, C18-SL, and C18:1-SL) and optionally a carrier.

A method of reducing the amount of sugar in an edible composition, said method comprising replacing an amount of sugar used in preparing an edible composition with an effective amount of at least one sophorolipid (e.g., selected from the group consisting of C16-SL, C18-SL, and C18:1-SL) and optionally a carrier, thereby reducing the sugar in an edible composition.

A method of reducing sugar intake of a subject, said method comprising replacing an amount of sugar used in preparing an edible composition with an effective amount of at least one sophorolipid (e.g., selected from the group consisting of C16-SL, C18-SL, and C18:1-SL) and optionally a carrier, thereby reducing the sugar intake of the subject.

A composition comprising: (I) at least one sophorolipid (e.g., selected from the group consisting of C16-SL, C18-SL, and C18:1-SL); and optionally a carrier; and (II) a bitter-tasting substance; wherein the total amount of at least one sophorolipid (e.g., selected from the group consisting of C16-SL, C18-SL, and C18:1-SL) is sufficient to reduce and/or mask the unpleasant taste of the bitter tasting substance.

A method for reducing and/or masking the bitter-taste of a bitter tasting substance comprising mixing: (I) at least one sophorolipid (e.g., selected from the group consisting of C16-SL, C18-SL, and C18:1-SL) and optionally a carrier; and (III) a bitter-tasting substance; wherein the total amount of at least one sophorolipid (e.g., selected from the group consisting of C16-SL, C18-SL, and C18:1-SL) is sufficient to reduce and/or mask the unpleasant taste of the bitter tasting substance.

A taste masked pharmaceutical liquid composition, comprising at least one sophorolipid (e.g., selected from the group consisting of C16-SL, C18-SL, and C18:1-SL) and optionally a carrier.

A method of reducing or alleviating bitter taste comprising adding at least one sophorolipid (e.g., selected from the group consisting of C16-SL, C18-SL, and C18:1-SL) and optionally a carrier to a composition for ingestion by humans or animals at a concentration effective to alleviate or reduce the bitter taste associated with the composition.

A flavoring system of a liquid or solid pharmaceutical composition, said system comprising at least one sophorolipid (e.g., selected from the group consisting of C16-SL, C18-SL, and C18:1-SL) and optionally a carrier; wherein the liquid or solid pharmaceutical composition comprises a pharmaceutically active agent, wherein said agent has a flavor profile that is undesirably high in bitter taste.

A composition comprising at least one sophorolipid (e.g., selected from the group consisting of C16-SL, C18-SL, and C18:1-SL) and optionally a carrier; and wherein the composition is edible and capable of reducing bitter taste of a bitter tastant. The composition, further comprising a bitter tastant.

A method of inhibiting or reducing the bitter taste due to a bitter tastant, wherein the method comprises placing at least one sophorolipid (e.g., selected from the group consisting of C16-SL, C18-SL, and C18:1-SL) and optionally a carrier, in the oral cavity of a subject. The method, wherein perception of the bitter taste in the oral cavity of the subject is eliminated. The method, wherein at least one sophorolipid (e.g., selected from the group consisting of C16-SL, C18-SL, and C18:1-SL) and optionally a carrier is ingested, in an effective amount, before, together with, or after the ingestion of a bitter tastant, to reduce the bitter taste of the bitter tastant.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Estimation of potency of sophorolipids based on responsive cell numbers.

|  | Concentration | %-responsive cells | Concentration adjusted response frequency |
|---|---|---|---|
| Sucralose | 5 mM | 16.67 | 16.67 |
| Sophorose | 292 uM | 16.05 | 274.89 |
| SL_OLE | 145 uM | 90.7 | 3127.59 |
| SL_PLM | 145 uM | 75.2 | 2593.10 |
| SL_STE | 145 uM | 59.4 | 2048.28 |
| Sucralose | 5 mM | 16.67 | 16.67 |
| Sophorose | 292 uM | 16.05 | 274.89 |
| SL_OLE | 145 uM | 90.7 | 3127.59 |

TABLE 1-continued

Estimation of potency of sophorolipids based on responsive cell numbers.

|  | Concentration | %-responsive cells | Concentration adjusted response frequency |
|---|---|---|---|
| SL_PLM | 145 uM | 75.2 | 2593.10 |
| SL_STE | 145 uM | 59.4 | 2048.28 |

We claim:

1. A method of inhibiting or reducing the bitter taste due to a bitter tastant, wherein the method comprises placing in the oral cavity of a subject an effective amount of a composition comprising at least one sophorolipid and optionally a carrier; wherein said sophorolipid is selected from the group consisting of C16-SL, C18-SL, C18:1-SL, and mixtures thereof.

2. A method of reducing bitter taste attributed to a bitter tastant in an edible composition, said method comprising adding to said edible composition an effective amount of at least one sophorolipid and optionally a carrier; such that any bitter taste induced by the bitter tastant is reduced; wherein said sophorolipid is selected from the group consisting of C16-SL, C18-SL, C18:1-SL, and mixtures thereof.

3. A method of inhibiting, reducing, or eliminating a bitter taste in a subject, said method comprising placing in the oral cavity of the subject an effective amount of at least one sophorolipid and optionally a carrier; wherein said sophorolipid is selected from the group consisting of C16-SL, C18-SL, C18:1-SL, and mixtures thereof.

4. A method of inhibiting a bitter taste receptor, said method comprising contacting the bitter taste receptor with a composition comprising an effective amount of at least one sophorolipid and optionally a carrier; wherein said sophorolipid is selected from the group consisting of C16-SL, C18-SL, C18:1-SL, and mixtures thereof.

5. The method according to claim 1, wherein said sophorolipid is C18:1-SL.

6. The method according to claim 2, wherein said sophorolipid is C18:1-SL.

7. The method according to claim 3, wherein said sophorolipid is C18:1-SL.

8. The method according to claim 4, wherein said sophorolipid is C18:1-SL.

9. The method of claim 2, wherein said edible composition is a food product.

10. The method of claim 9, wherein said sophorolipid is C18:1-SL.

* * * * *